United States Patent
Alqathami

(10) Patent No.: US 10,307,494 B2
(45) Date of Patent: Jun. 4, 2019

(54) CURABLE COMPOSITION AND METHOD FOR IMPLANTATION

(71) Applicants: National Guard Health Affairs, Riyadh (SA); King Saud bin Abdulaziz University for Health Sciences, Riyadh (SA); King Abdullah International Medical Research Center, Riyadh (SA)

(72) Inventor: Mamdooh Alqathami, Riyadh (SA)

(73) Assignees: National Guard Health Affairs, Riyadh (SA); King Saud bin Abdulaziz University for Health Sciences, Riyadh (SA); King Abdullah International Medical Research Center, Riyadh (SA)

( * ) Notice: Subject to any disclaimer, the term of this patent is extended or adjusted under 35 U.S.C. 154(b) by 389 days.

(21) Appl. No.: 15/195,116

(22) Filed: Jun. 28, 2016

(65) Prior Publication Data

US 2017/0368206 A1    Dec. 28, 2017

(51) Int. Cl.
| | |
|---|---|
| *A61K 49/18* | (2006.01) |
| *A61K 49/12* | (2006.01) |
| *A61K 51/06* | (2006.01) |
| *A61K 51/12* | (2006.01) |

(52) U.S. Cl.
CPC .......... *A61K 49/1818* (2013.01); *A61K 49/12* (2013.01); *A61K 51/06* (2013.01); *A61K 51/1213* (2013.01); *A61K 51/1282* (2013.01)

(58) Field of Classification Search
None
See application file for complete search history.

(56) References Cited

U.S. PATENT DOCUMENTS

| | | | | |
|---|---|---|---|---|
| 7,776,351 | B2 * | 8/2010 | Benz .................. | A61L 27/18 424/422 |
| 2005/0220714 | A1 | 10/2005 | Kauzlarich et al. | |

FOREIGN PATENT DOCUMENTS

| | | |
|---|---|---|
| CN | 104258423 A | 7/2015 |
| CN | 104784707 A | 7/2015 |
| KR | 2012072404 A | 7/2012 |

\* cited by examiner

*Primary Examiner* — Michael G. Hartley
*Assistant Examiner* — Jennifer Lamberski
(74) *Attorney, Agent, or Firm* — Oblon, McClelland, Maier & Neustadt, L.L.P.

(57) ABSTRACT

A biocompatible curable composition and a method of detecting a border of a tumor, a tissue of interest, or both including injecting the biocompatible curable composition and contacting the border of a tumor or a tissue, the biocompatible curable composition crosslinks to form a three-dimensional cured nanocomposite, and imaging the three-dimensional (3D) cured nanocomposite, and imaging the 3D cured nanocomposite by at least one of MRI, CT, ultrasound, and X-ray, to detect the border of the tumor or the tissue of interest or track tumor motion during radiotherapy treatment. The biocompatible curable composition comprising an organic polymer having a hydrolysable functional group, a metallic nanoparticle, and a polar or a non-polar solvent. A brachytherapy strand consisting of a biocompatible curable composition and a radio-isotope seed. The biocompatible curable composition is shaped into an elongated cylinder and forms a 3D cured nanocomposite with a radio-isotope seed embedded.

19 Claims, 15 Drawing Sheets

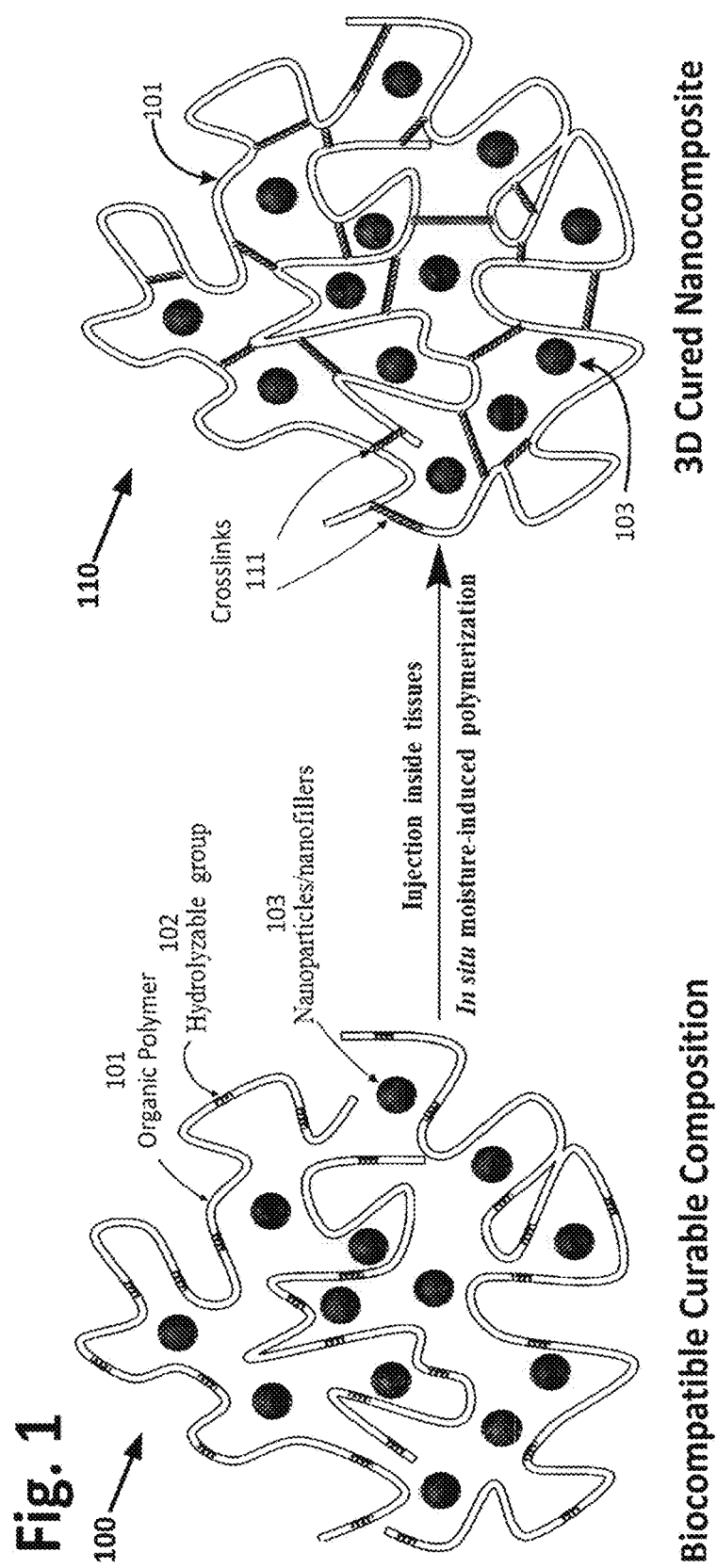

214

200

216

218

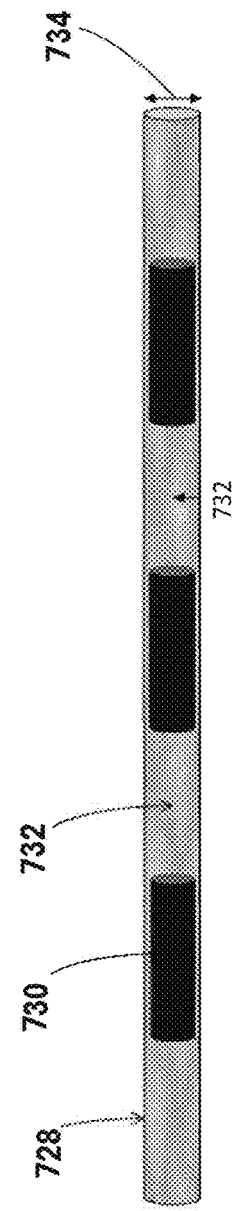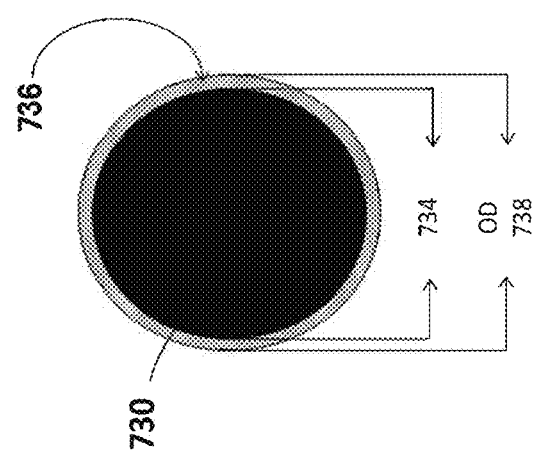
Fig. 7A
Fig. 7B

CURABLE COMPOSITION AND METHOD FOR IMPLANTATION

BACKGROUND OF THE INVENTION

Technical Field

The present disclosure relates to a moisture curable polymer that is biocompatible and suitable for use in surgical applications and radiotherapy as a fiducial marker, a tissue spacer, or a brachytherapy seed spacer and marker.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Conventional radiotherapy aims to control tumor infiltration, whereas surgery is sometimes necessary to control the bulky tumor volume. Modern radiotherapy delivery techniques can control both tumor infiltration and the bulky tumor by irradiating tumors with higher doses of radiation and greater spatial selectivity (localization) thus sparing surrounding normal tissues from radiation damage. In order to control tumor infiltration, the treatment beam needs to be accurately positioned with respect to the tumor. In recent years, image-guided radiotherapy (IGRT) has been integrated into the majority of radiotherapy treatment delivery machines. IGRT is currently a key component of modern radiotherapy treatments. Conventional approaches to image guidance involve preoperative images (mainly CT scans) registered (i.e. image correlation to field of view) intraoperatively to the reference frame of the patient and navigation system by co-localization of fiducial markers affixed to the patient. At least three (and commonly six to 12) fiducials are necessary to provide accurate registration. The navigation system can then provide a virtual representation of tools in real-time within the context of the preoperative image data.

Recent advancements in IGRT have allowed for the increase in radiation (also known as dose escalation) dose delivery to malignant tumors leading to better tumor control than ever before. However, the downside of dose escalation is the potential increase in toxicity to adjacent organs at risk. One typical example is the potential rectal damage as a result of dose escalation in prostate radiotherapy in which the rectum is considered a sensitive critical surrounding structure. In order to minimize toxicity in dose escalation regimens, inter- and intra-fractional target motion must be taken into account before the delivery of the radiation dose. Organs such as the prostate are susceptible to deformation and motion which can be attributed to physical internal organ movements, breathing, weight loss and uncertainties related to patient setups. Accounting for these motion-related deviations would allow the delivery of the desired dose coverage of the target volumes whilst minimizing unnecessary dose to normal organs. Further, accounting for the deviations would allow a physician to prescribe tighter treatment margins around the tumor, possibly reducing the dose to normal tissues.

Due to the increase in IGRT treatments, various techniques have been explored to assist in tracking the location of tumors and surrounding critical structures. The most commonly used technique involves implantation of fiducial markers as surrogates of the target volumes with the linear accelerator (LINAC) built-in kilovoltage or megavoltage imaging systems. However, computed tomography (CT) images are limited in terms of detail and show only information about the bony anatomical structures. For many clinical applications, the image quality of these CT scans is not sufficient to accurately distinguish the tumor from surrounding healthy tissues. This has steered an extensive research and development in the integration of magnetic resonance imaging (MRI) into modern radiotherapy treatment systems as an alternative to CT.

The use of MRI for the guidance of radiotherapy has revolutionized diagnostics imaging due to excellent soft tissue contrast. This clearly makes MRI well suited for radiotherapy, both in the definition of tumor geometry and the characterization of its functional information.

Tissue characteristics can be imaged by determining the concentration (or density) of hydrogen (H1) protons within the tissue and weighting (T1 or T2-weighted imaging). For example, tissues with high proton contents (e.g., fat) will produce strong signals and have a bright appearance on T1-weighted images. Therefore, the MR image is an image of H1 protons. When tissues that contain hydrogen (i.e., protons) are subjected to a magnetic field, some of the proton nuclei spins align in the same direction as the magnetic field. This alignment produces the magnetization in the tissue, which then emits a radio-frequency signal. Tissues that do not have an adequate concentration of hydrogen are not visible on MRI.

The MR-Linac (MRL) combines two advanced technologies—an MRI scanner and a linear accelerator—to precisely locate tumors in real-time, and adapt the shape of the X-ray beams in real time to conform to the shape of the tumor. MRL is a new technology with few prototype systems being tested for clinical use worldwide. See patents Nos: WO 2009113069A1, WO 2014044635A1, U.S. Pat. Nos. 9,155,913 B2, 8,331,531 B2, and US 20140135615 A1, each incorporated herein by reference in its entirety.

However, the location of tumors, as well as normal tissues and organs at risk inside the body, change frequently. For example, lung tumor/s will move up and down during the patient's breathing. The location of prostate tumors changes from day-to-day depending on fullness of the bowel and bladder of the patient during radiotherapy treatment. Therefore, there is still a risk of the tumor shifting location, which increases the probability of delivering unnecessary radiation dose to adjacent healthy tissues or organs.

Precise adaptive radiotherapy guided by real-time MRI images could prove a significant advance in radiation oncology in general if the daily location of tumors and its proximity to surrounding critical structures can be accurately determined. To overcome this challenge, a minimally invasive MRI-visible marker system would significantly improve the efficiency of MRI-guided radiotherapy. Such a minimally invasive MRI-visible marker will also enable the constant monitoring of tumor movement during treatment by acting as image registration surrogates for indicating the position of the treatment volumes and also, the precise targeting of moving tumors and avoidance of healthy surrounding tissues. MRI contrast depends on the biologically variable parameters of proton density; longitudinal relaxation time (T1), and transverse relaxation time (T2), variable image contrast can be achieved by using different pulse sequences and by changing the imaging parameters. Signal intensities on T1, T2, and proton density-weighted images relate to specific tissue characteristics. Therefore, a key requirement for an MRI-visible marker system is to have a different MRI signal intensity to that of normal tissues. This will enable the markers to be clearly distinguished from normal tissues and also, enable them to be used for tumor tracking and daily pre-treatment quality assurance procedures.

Further, current brachytherapy seeds and spacer technologies involves attaching a polymer (with or without encapsulated liquid contrast agent) to brachytherapy seeds by some form of adhesive such as cyanoacrylate adhesives or polymer thread such as polyurethanes. See US 20100324353 A1, Adhesive-stiffened brachytherapy strand, Kevin Helle, et al, Dec. 23, 2010; and US 20150375011, Brachytherapy Seed Insertion and Fixation System, John Spittle, Dec. 31, 2015, each incorporated herein by reference in its entirety. However, one shortcoming of such adhesive technologies is that they are fragile considering the size of the seeds and usually susceptible to breakage during the implantation process or post-implantation. Saibishkumar et al., 2009 compared stranded seeds (SSs) with loose seeds (LSs) in terms of seed loss after $^{125}$I prostate brachytherapy. See Saibishkumar E P et al., 2009 Sequential Comparison of Seed Loss and Prostate Dosimetry of Stranded Seeds With Loose Seeds in 125I Permanent Implant for Low-Risk Prostate Cancer Int. J. Radiat. Oncol. Biol. Phys. 73 61-8, incorporated herein by reference in its entirety. The preceding references observed greater seed loss with SSs compared with LSs, with the primary site of loss being the urinary tract. Therefore, a more durable seed-spacer attachment system is highly desirable to minimize breakage and migration of commercial radioactive seeds. Assigned patent application pub. No US 20140178297 A1 describes a contrast marker and a spacer comprising a liquid Cobalt-based compound [$(CoCl_2)_n(C_2H_5NO_2)_{1-n}$] encased in a polymer, incorporated by reference herein in its entirety. Assigned patent application pub. No U.S. Pat. No. 8,821,835B2 describes a brachytherapy spacer where therapeutic agents can be encapsulated within cylindrical shape objects. See U.S. Pat. No. 8,821,835 B2, "Flexible and/or elastic brachytherapy seed or strand," Edward J. Kaplan, Sep. 2, 2014, incorporated herein by reference in its entirety. A polymer that can withstand the natural motion of tumors and tissues, and prevent risk due to breakage of brachytherapy seeds by creating a tight seal around the seed, is of value to the medical radiotherapy field.

In view of the forgoing, one objective of the present disclosure is to provide a biocompatible curable composition which includes metallic nanoparticles and is cured in situ upon contact with moisture to provide a fiducial marker which is visible by an imaging modality and useful in radiation therapy.

BRIEF SUMMARY OF THE INVENTION

According to a first aspect, the present disclosure relates to a method of detecting a border of a tumor, a tissue of interest, or both including injecting the biocompatible curable composition into a subject and contacting the border of a tumor, a tissue of interest, or both, wherein the biocompatible curable composition crosslinks upon exposure to an aqueous solution or moisture to form a three-dimensional cured nanocomposite, which is implanted by a covalent bond to the border of the tumor, the tissue of interest, or both, and imaging the three-dimensional cured nanocomposite by at least one of magnetic resonance imaging, computed tomography, ultrasound, and X-ray, to detect the border of the tumor, the tissue of interest, or both.

In some implementations of the method, the biocompatible curable composition comprises an organic polymer comprising at least one hydrolysable functional group selected from a silane and an isocyanate, a metallic nanoparticle, and a solvent selected from the group consisting of hexane or toluene. The metallic nanoparticle is at least one of a manganese-based nanoparticle and a gadolinium-based nanoparticle and is dispersed in the organic polymer and solvent at a weight percent relative to the total weight of the biocompatible curable composition of 0.1% to 30%.

In some implementations of the method, the metallic nanoparticle has at least one dimension of 1 nm-150 nm.

In some implementations of the method, the metallic nanoparticle is modified by at least one of an organic ligand, a coupling agent, and a surfactant.

In some implementations of the method, the three-dimensional cured nanocomposite is an elastomeric three-dimensional cured nanocomposite.

In some implementations of the method, the imaging further comprising registering the image of the three-dimensional cured nanocomposite at the border of a tumor, a tissue of interest, or both.

In some implementations of the method, the method further includes a second injecting of a radio-isotope seed into the three-dimensional cured nanocomposite after the injecting or after the imaging.

According to a second aspect, the present disclosure relates to a biocompatible curable composition comprising an organic polymer comprising at least one hydrolysable functional group selected from a silane and an isocyanate, a metallic nanoparticle, and a solvent selected from the group consisting of hexane or toluene. The metallic nanoparticle is at least one of a manganese-based nanoparticle and a gadolinium-based nanoparticle, and is dispersed in the organic polymer and solvent. The biocompatible curable composition crosslinks upon contact with an aqueous solution or moisture to form a three-dimensional cured nanocomposite.

In some embodiments of the biocompatible curable composition, the metallic nanoparticle has at least one dimension of 1 nm-150 nm.

In some embodiments of the biocompatible curable composition, the metallic nanoparticle is 0.1-30 wt. % relative to the total weight of the biocompatible curable composition.

In some embodiments of the biocompatible curable composition, the metallic nanoparticle is modified by at least one of an organic ligand, a coupling agent, and a surfactant.

In some embodiments of the biocompatible curable composition, the biocompatible curable composition and the three-dimensional cured nanocomposite is detectable by at least one imaging modality selected from the group consisting of magnetic resonance imaging, computed tomography, ultrasound, and X-ray.

In some embodiments, the biocompatible curable composition further includes a second nanoparticle having at least one of a paramagnetic element, a radio-isotope, a radio-opaque element, and a radio-opaque compound.

In some embodiments of the biocompatible curable composition, the second nanoparticle is a radio-isotope seed.

In some embodiments of the biocompatible curable composition, the three-dimensional cured nanocomposite is an elastomeric three-dimensional cured nanocomposite.

In some embodiments of the biocompatible curable composition, the elastomeric three-dimensional cured nanocomposite crosslinks a biological tissue via the hydrolysable functional groups.

In some embodiments of the biocompatible curable composition, the elastomeric three-dimensional cured nanocomposite has a Shore durometer hardness of 5 to 40 on a Shore durometer Type A scale, or a Shore durometer hardness of 40-100 on a Shore durometer Type OO scale.

In some embodiments of the biocompatible curable composition, the organic polymer comprises at least one reacted form of a tetraethoxysilane, a methyltrimethoxysilane, a methyltriethoxysilane, an isobutyltrimethoxysilane, a phenyl trimethoxysilane, and a n-octyltriethoxysilane.

According to a third aspect, the present disclosure relates to a brachytherapy strand consisting of biocompatible curable composition and a radio-isotope seed. The biocompatible curable composition is in the form of an elongated cylinder and crosslinks upon contact with an aqueous solution or moisture to form a three-dimensional cured nanocomposite having the radio-isotope seed embedded in the three-dimensional cured nanocomposite.

In some embodiments of the brachytherapy strand the biocompatible curable composition includes an organic polymer comprising at least one hydrolysable functional group selected from a silane and an isocyanate, a solvent selected from the group consisting of hexane or toluene, and a metallic nanoparticle. The metallic nanoparticle is at least one of a manganese-based nanoparticle and a gadolinium-based nanoparticle, is dispersed in the organic polymer and the solvent, and is visible by MRI.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 1 is a chemical scheme illustrating the mechanism of cross-linking of the disclosed biocompatible curable composition;

FIG. 7A is an illustrative side view diagram showing the disclosed embedded/stranded brachytherapy seeds device;

FIG. 7B is an illustrative axial view diagram showing the disclosed embedded/stranded brachytherapy seeds device;

DETAILED DESCRIPTION OF THE EMBODIMENTS

Figure 2A:
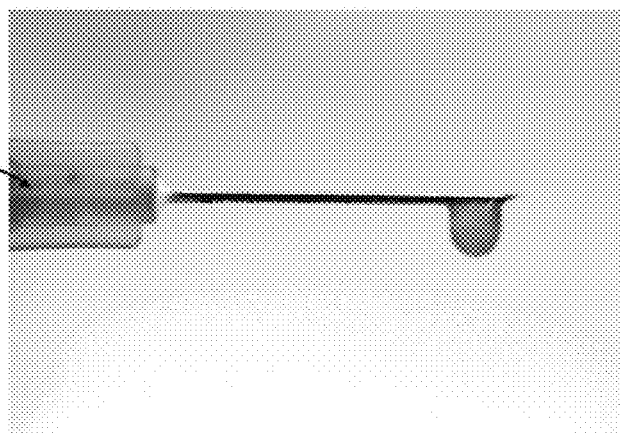
FIG. 2A is a set of illustrative photographs showing: the biocompatible curable composition being injected from a 25 G needle 214 (top)

As referred to herein, "biocompatible" may be defined as a substance that is compatible with living tissue or a living system by not being toxic, injurious, or physiologically reactive and not causing immunological rejection.

A "nanoparticle" as referred to herein may be particles with at least one dimension of less than 100 nm.

Throughout the specification ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

An aspect of the present disclosure relates to a method of detecting a border of a tumor, a tissue of interest, or both. The method includes injecting the biocompatible curable composition into a subject and contacting the biocompatible curable composition with the border of a tumor, a tissue of interest, or both. The biocompatible curable composition crosslinks upon exposure to an aqueous solution or moisture to form a three-dimensional (3D) cured nanocomposite, which is implanted by a covalent bond to the border of the tumor, the tissue of interest, or both. After the biocompatible curable composition is injected, the 3D cured nanocomposite is imaged by at least one of magnetic resonance imaging (MRI), computed tomography (CT), ultrasound, and X-ray, wherein the border of the tumor, the tissue of interest, or both is detected.

A further aspect of the present disclosure relates to the biocompatible curable composition. The biocompatible curable composition comprises an organic polymer comprising at least one hydrolysable functional group selected from a silane and an isocyanate, a metallic nanoparticle, and a polar or a non-polar solvent selected from the group consisting of water, methanol, isopropanol, hexane or toluene. The organic polymer may include any polymer composition having one or more hydrolysable silane groups that, in the presence of water (or moisture), undergoes hydrolysis to silanols (Si—OH) and crosslinks via the formation of siloxane groups (—Si—O—Si—) between polymer chains as depicted in the scheme below. The scheme depicts a polysiloxane hydrolysed at a single hydrolysable group, however up to three hydrolysable groups may be included to provide for branch points during crosslinking:

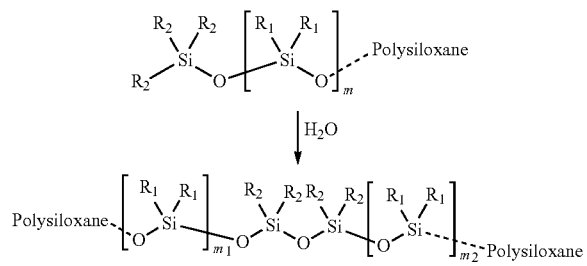

$R_1$=Each independently selected from methyl, ethyl, propyl, isopropyl, and higher branched and straight aliphatic chains, aromatic group and substituted aromatic group which may include heteroatoms such as nitrogen, sulfur, and halogens; $R_2$=each independently selected from the groups listed for $R_1$, with at least 1 $R_2$ selected from a hydrolysable groups, such as acetoxy, methoxy, alkoxy, oximino, ethoxy or amino; $m_1$, $m_2$, m>1, and each individually represents a polysiloxane component of the linear or branched copolymer that constitutes the organic polymer FIG. 1 depicts a schematic of the biocompatible curable composition 100 crosslinking upon contact with an aqueous solution or moisture to form a 3D cured nanocomposite 110. The biocompatible curable composition 100 is depicted with the organic polymer having hydrolysable functional groups ("hydrolysable group") 102 and including metal nanoparticles or nanofillers 103 interspersed in the biocompatible curable composition. The crosslinkages 111 which is a result of isocyanate and/or a silane is depicted in FIG. 1. The hydrolysable groups 102 form the crosslinks 111 upon contact with moisture or aqueous solution.

A first isocyanate group forms a urea linkage with a second isocyanate group through a two-step process including a hydrolysis to form and amine on the main chain and releasing a carbon dioxide, followed by the formation of the urea bond with another isocyanate functional group. An isocyanate may form a carbamate bond with a silanol extending from a polysiloxane. An exemplary scheme of the polyisocyanate formation is shown below:

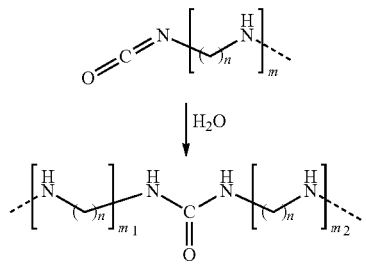

n>1
$m_1$, $m_2$, m >1, and each individually represents a polyisocyanate component of the linear or branched copolymer.

In some embodiments, an isocyanate may form a carbamate bond with a silanol of the organic polymer of the present disclosure. In some embodiments, a polysiloxane may form a block copolymer with a polyisocyanate. In some embodiments, an isocyanate functional group on the organic polymer may facilitate the crosslinking of the 3D cured nanocomposite to an amine on the surface of a biological tissue.

Figure 2B:
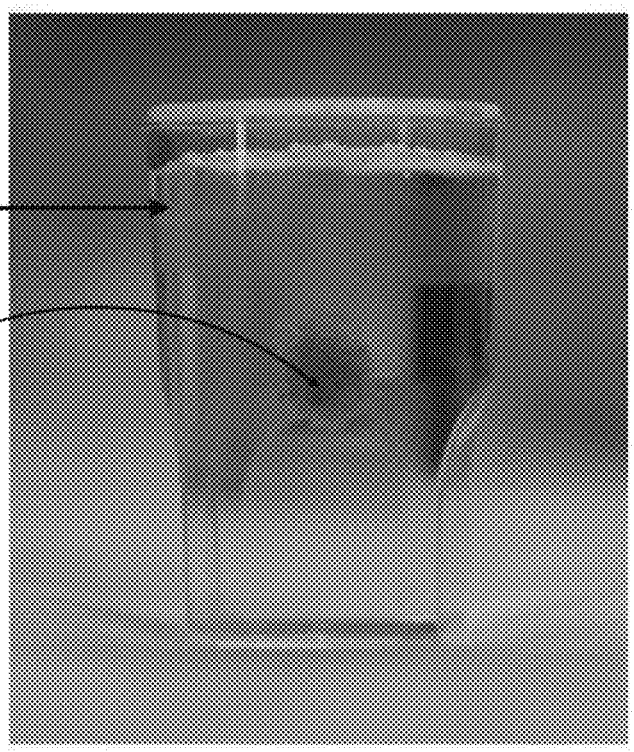
FIG. 2B is an image of the 3D cured nanocomposite 216 immediately after injection into a gelatinous phantom.
Figure 2C:
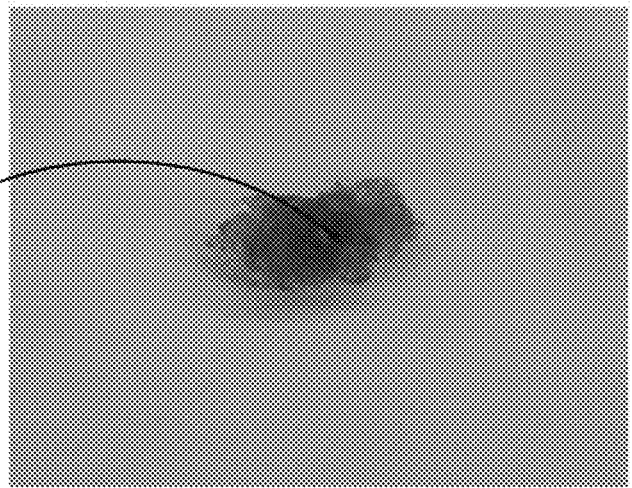
FIG. 2C is an image of an excised 3D cured nanocomposite 218 one hour later.
Figure 3A:
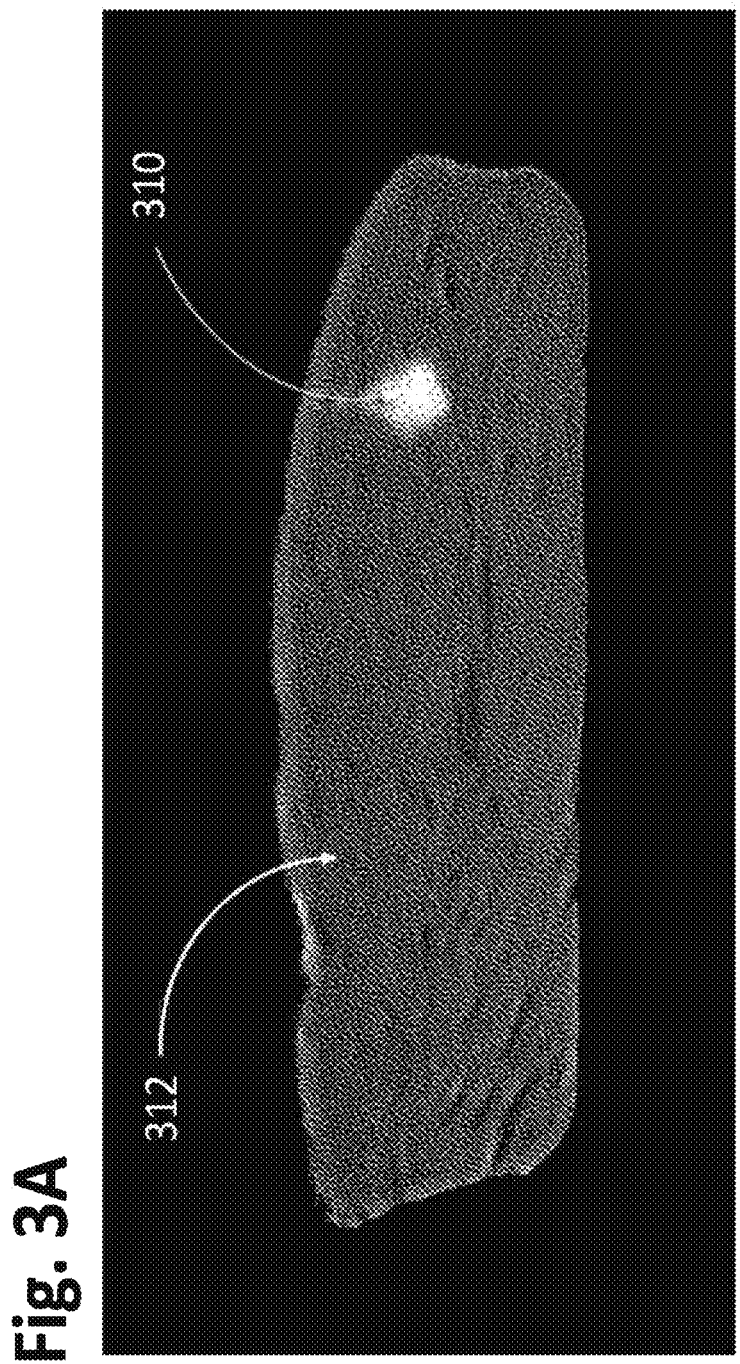
FIG. 3A is a sagittal view of a T1-weighted MRI image showing an in situ cross-linked nanocomposite marker 310 approximately one hour after injection in raw meat (tissue) 312.

The composition disclosed herein comprises a biocompatible curable composition 100 that cures via crosslinking 111 from a liquid phase to a three-dimensional (3D) elastomeric and cross-linked nanocomposite 110 solid phase state upon contact with water or moisture. The term elastomer used herein refers to materials that show elastic properties. In FIG. 1, the nanocomposite 110 contains nanoparticles 103 that render the nanocomposite 110 visible under at MRI, CT and ultrasound. The biocompatible curable composition is cross-linked and shaped in situ 210 upon contact with the moisture in tissue's 212, as shown in FIG. 2A-FIG. 2C. Upon cross-linking, the biocompatible curable composition forms an elastomeric 3D nanocomposite 110 that adheres and conforms to the surrounding tissues. The biocompatible curable composition can be easily injected through very narrow diameter needles (e.g., 25 gauge needle) as shown in FIG. 3A, making the injection procedure minimally invasive.

In some embodiments, the organic polymer may comprise a backbone having hydrolysable functional groups such as, but not limited to methoxy, ethoxy, acetoxy, enoxy, oximino, amino, alkoxy, acyloxy, or halo. The previously mentioned hydrolysable functional groups may form byproducts upon crosslinking such as, but not limited to acetic acid, methanol and ethanol. Examples of the organic polymers may be, but are not limited to polyalkoxysilanes (e.g. methoxysilanes, ethoxysilanes, etc.), polyaminosilanes, polyesters, poly(tetraethoxysilane), poly(methyltrimethoxysilane), poly(methyltriethoxysilane), poly(isobutyltrimethoxysilane), poly (phenyl trimethoxysilane), poly(n-octyltriethoxysilane), poly(glycolic acid), poly(lactic acid), poly(caprolactone), poly(lactic-co-glycolic acid), poly(butylene succinate), poly (trimethylene carbonate), poly(p-dioxanone), poly(butylene terephthalate). The exemplary list of polymers may be functionalized by hydrolysable functional groups as described herein. In some embodiments, a non-hydrolysable (not moisture sensitive) organic polymer may be further included in the organic polymer chain, part of the side chains, or in a mixture with the organic polymer and included in the biocompatible curable composition. Exemplary non-hydrolysable organic polymer may include, but is not limited to polyester amides, polyanhydrides, polyphosphoesters, polyurethanes, polyalkyl cyanoacrylates, polyethers, polysiloxanes, polyesters, polybutyl cyanoacrylate, polyethylene glycol, polyortho esters, poly(bis(hydroxyethyl)terephthalate-ethylorthophosphorylate), poly[(carboxyphenoxy)propane-sebacic] acid, poly[bis(hydroxyethyl)], terephthalate-ethyl, poly(dimethylsiloxane-co-diphenylsiloxane), dihydroxy terminated-poly(dimethylsiloxane-co-alkylmethylsiloxane), poly(methylphenylsiloxane) and polydimethylsiloxane. In some embodiments, the organic polymer may further include, in a mixture, additional biocompatible moisture-cure polymer compositions useful for the practice of the present invention may be selected from those described in assigned patent application publications. See WO 2011150199 A2, One-part moisture-curable tissue sealant, Eric J. Beckman, Dec. 1, 2011; WO 2000043432 A1 Moisture curable polyurethane compositions, Brian W Carlson et al, Jul. 27, 2000; U.S. Pat. No. 7,943,698 B2, Moisture cure alpha-silane modified acrylic coatings, Richard F. Tomko, May 17, 2011; WO 2004100926 A2, Delivery of agents using hydrolysable leaving groups, Michael E Benz, Nov. 25, 2004; U.S. Pat. No. 8,088,940 B2, Hydrolysable silanes of low VOC-generating potential and resinous compositions containing same, Misty W. Huang et al, Jan. 3, 2012; US 20100010166 A1, Silane-terminated prepolymers and relative adhesive sealant formulations, Alessandro Galbiati et al, Jan. 14, 2010, each incorporated herein by reference in its entirety. A ratio of non-hydrolysable functional groups in the side-chains relative to hydrolysable functional groups in the polymer backbone may be from about 1:1000-1:2, about 1:100-9:20, about 1:20-4:10, about 1:10-3:10, or about 3:20-1:4.

In some embodiments, the organic polymer may be modified to include a biodegradable functional group such as a thiol, a disulfide, an amine, an ammonium ion, a carboxylic acid, a phosphine, a phosphate, a carboxylate, a silane, a sulfonate, an amide and a phosphonate. The biodegradable functional groups may be included at a weight percent relative to the total weight of the organic polymer of 0.1% to 30%, about 0.5% to 28%, about 1% to 25%, about 5% to 22%, about 10% to 20%, or about 15% to 18%.

In some embodiments, upon curing, the biocompatible curable composition forms a 3D cured nanocomposite, which is an elastomeric 3D cured nanocomposite. An elastomer is a polymer with viscoelasticity (having both viscosity and elasticity) and very weak inter-molecular forces, generally having low Young's modulus and high failure strain compared with other materials. Each of the monomers which link to form the polymer is usually made of carbon, hydrogen, oxygen or silicon. Elastomers are amorphous polymers existing above their glass transition temperature, so that considerable segmental motion is possible. For example, the 3D cured nanocomposite may be molded and cross-linked ex vivo into an elastic fiducial marker a shape including, but not limited to a cylinder, a disk, or a polygonic shape. In some embodiments, the elastomeric 3D cured composite shape may have at least one dimension of about 0.5 mm-10 mm, about 1 mm-8 mm, or about 5 mm-6 mm.

In some embodiments, the biocompatible curable composition in cured form has a viscosity at room temperature of 5000 to 20000 centipoise (cps), 6000 cps to 18000 cps, 8000 cps to 16000 cps, or 10000 cps to 14000 cps. Viscosity may be controlled by modifying the chemical structure or the inclusion of nanofiller to the biocompatible curable composition, as described herein. The polymers employed in the composition of the present disclosure may be characterized by a variety of factors such as MRI visibility. The extent to which polymers are visible on T1 MRI depends on a number of factors: (1) the percentage composition (number) of hydrogen protons within the polymers. For example, polymers rich in hydrogen protons are visible of T1 MRI and usually give similar signal intensity to that of normal tissues, and (2) the degree of mobility of protons within the polymer matrix. For example, RF signal intensity, and image brightness are determined by the proton atoms resonance when subjected to a magnetic field. Polymers with no (or limited) degree of proton mobility (i.e. hard polymers) may consist of only hard segments and are not deformable. Hard polymers may contain rigid groups such aromatic groups, bulky side-chains such as tertiary butyl groups, polar groups such as ester and hydrogen bonding groups such as hydroxyl. These hard polymers may not show any measurable MRI signal and are therefore not suitable for the practice of this present disclosure. Polymers with a hydrogen content 30% to 50%, 35%-45%, or 38%-42% and proton mobility (e.g. acidic protons, hydrogen bonding protons) are more suitable for the practice of the present disclosure including elastomers, and elastomeric polymers as described herein.

The hardness of the biocompatible curable composition after it is cured into the 3D cured nanocomposite may be measured by a Shore durometer. The Shore durometer hardness scale is a one of several measures of the hardness of a material. Hardness may be defined as a material's resistance to permanent indentation. The durometer scale was defined by Albert Ferdinand Shore, who developed a device to measure Shore hardness in the 1920s. The term durometer is often used to refer to the measurement as well as the instrument itself. Durometer is typically used as a measure of hardness in polymers, elastomers, and rubbers. There are several scales of durometer, used for materials with different properties. The two most common scales, using slightly different measurement systems, are the ASTM D2240 type A and type D scales. The A scale is for softer plastics, while the D scale is for harder ones. However, the ASTM D2240-00 testing standard calls for a total of 12 scales, depending on the intended use; types A, B, C, D, DO, E, M, O, OO, OOO, OOO-S, and R. Each scale results in a value between 0 and 100, with higher values indicating a harder material. Durometer, like many other hardness tests, measures the depth of an indentation in the material created by a given force on a standardized presser foot. This depth is dependent on the hardness of the material, its viscoelastic properties, the shape of the presser foot, and the duration of the test. ASTM D2240 durometers allows for a measurement of the initial hardness, or the indentation hardness after a given period of time. The basic test requires applying the force in a consistent manner, without shock, and measuring the hardness (depth of the indentation). If a timed hardness is desired, force is applied for the required time and then read. The material under test should be a minimum of 6.4 mm (0.25 inches) thick. In some embodiments of the biocompatible curable composition, the elastomeric three-dimensional cured nanocomposite has a Shore durometer hardness of about 5 to 40, about 8-35, about 10-30, about 15-25, or about 18-22 on a Shore durometer Type A scale; or a Shore durometer hardness of about 40-100, about 50-90, about 60-80, or about 65-75 on a Shore durometer Type OO scale.

In some embodiments, the hydrolysable functional groups may crosslink with a tissue, an organ surface, across polymer chains, or a combination thereof. In some embodiments, a hydrolysable functional group on a side chain of the organic polymer may crosslink with a backbone of the organic polymer. The hydrolysable functional groups may crosslink with a tumor, a tissue and/or the organ surface via amide bond, ester bond, disulfide bond, a nitrogen-silicon bond (forming an aminosilane), or a combination thereof. In some embodiments the polymer backbone or side chain may form an ionic or electrostatic interaction to the tissue and/or the organ surface. In some embodiments the polymer backbone or side chain may form a crosslinking mediated by at least one of a monovalent or polyvalent metal. The monovalent or polyvalent metal may be, but is not limited to magnesium, calcium, cobalt, manganese, nickel, copper, zinc, and iron. In some embodiments, crosslinking may be mediated by a native enzyme in the tissue, such as, but not limited to collagenase or transglutaminase.

The metallic nanoparticle included in the biocompatible curable composition is at least one of a manganese-based nanoparticle and a gadolinium-based nanoparticle and is dispersed in the organic polymer and solvent at a weight percent relative to the total weight of the biocompatible curable composition of about 0.1% to 30%, about 0.5% to 28%, about 1% to 25%, about 5% to 20%, or about 10% to 15%. Nanoparticles, which may also include a nanopowder, a nanocluster, or a nanocrystal, may refer to a microscopic particle with at least one dimension of about 1 nm-150 nm, about 5 nm-140 nm, about 10 nm-130 nm, about 25 nm-120 nm, about 50 nm-110 nm, about 75 nm-100 nm, or about 80 nm-90 nm. A feature of nanoparticles, as opposed to bulk macroscale materials which have constant physical properties regardless of its size, is that the nanoparticles size often dictates the physical and chemical properties. Thus, the properties of materials change as their size approaches the nanoscale and as the percentage of atoms at the surface of a material becomes significant. Nanoscale materials also have a large surface area for a given volume compared to bulk materials.

The metallic nanoparticles described herein may have an atomic number (Z) of more than 25. The metallic nanoparticle may further include, but is not limited to gold, silver, platinum, palladium, cobalt, iron, copper, tin, tantalum, vanadium, gadolinium, manganese, molybdenum, osmium, iridium, rhenium, hafnium, thallium, bismuth, and dysprosium. In some embodiments of the biocompatible curable composition, paramagnetic nanoparticles may be included. Paramagnetic elements have an unpaired electron. The unpaired electron has a magnetic moment which is about 1000 times that of a proton. The magnetic moment leads to a rapid change in a local magnetic field. Dipoles of unpaired electrons have a considerably stronger magnetic susceptibility when they are located in densely packed crystalline structures, such as nanoparticles. Paramagnetic particles are visible in magnetic spectroscopy such as magnetic resonance imaging. In some embodiments, manganese and gadolinium-based nanoparticles are preferred in the biocompatible curable composition as paramagnetic nanoparticles.

In some embodiments, the biocompatible curable composition further includes a second nanoparticle having at least one of a paramagnetic element, a radio-isotope, a radio-opaque element, and a radio-opaque compound. The paramagnetic element of the second nanoparticle may be as described herein of the metallic nanoparticle. Further, the radio-isotope is a radioactive isotope of an element. Different isotopes of the same element have the same number of protons in their atomic nuclei but differing numbers of neutrons. They can also be defined as atoms that contain an unstable combination of neutrons and protons. Nuclear medicine uses radiation via radio-isotopes to provide diagnostic information about the functioning of a person's specific organs, or to treat them. Diagnostic procedures using radio-isotopes are now routinely employed in medicine. Radiotherapy can be used to treat some medical conditions, especially cancer, using radiation to weaken or destroy particular targeted cells. Radio-isotopes that may be included in the biocompatible curable composition include, but are not limited to fluorine-18, gallium-67, krypton-81m, rubidium-82, nitrogen-13, technetium-99m, indium-111, iodine-123, xenon-133, thallium-201, yttrium-90, and iodine-131. The radio opaque refers to the relative inability of electromagnetic radiation, particularly X-rays, to pass through a particular material. Materials that inhibit the passage of electromagnetic radiation are called radiodense or radiopaque, while those that allow radiation to pass more freely are referred to as radiolucent. The radio opaque element may include, but is not limited to bismuth, barium, and tungsten and the radio opaque compound may include, but is not limited to bismuth trioxide, bismuth oxychloride, bismuth subcarbonate, and barium sulfate. The secondary nanoparticle included in the biocompatible curable composition may be dispersed in the organic polymer and solvent at a weight percent relative to the total weight of the biocompatible curable composition of about 0.1% to 30%, about 0.5% to 28%, about 1% to 25%, about 5% to 20%, or about 10% to 15%. The metallic nanoparticle and the secondary nanoparticle may be in a ratio relative to each other of 1:1 to 15:1, 2:1 to 10:1, or 5:1-7:1.

The sensitivities of instrumentation may improve in the future however at with present technology the concentration of nanoparticles incorporated within the polymer matrix of the nanocomposite depends on the diagnostic used. For example, for MRI visibility, paramagnetic nanoparticles with a concentration of, but not limited to 0.1-2 mM is acceptable for use in the biocompatible curable composition. For X-ray visibility (e.g., CT) at a concentration of, but not limited to 100-900 mM is acceptable for use in the biocompatible curable composition.

Figure 3B:
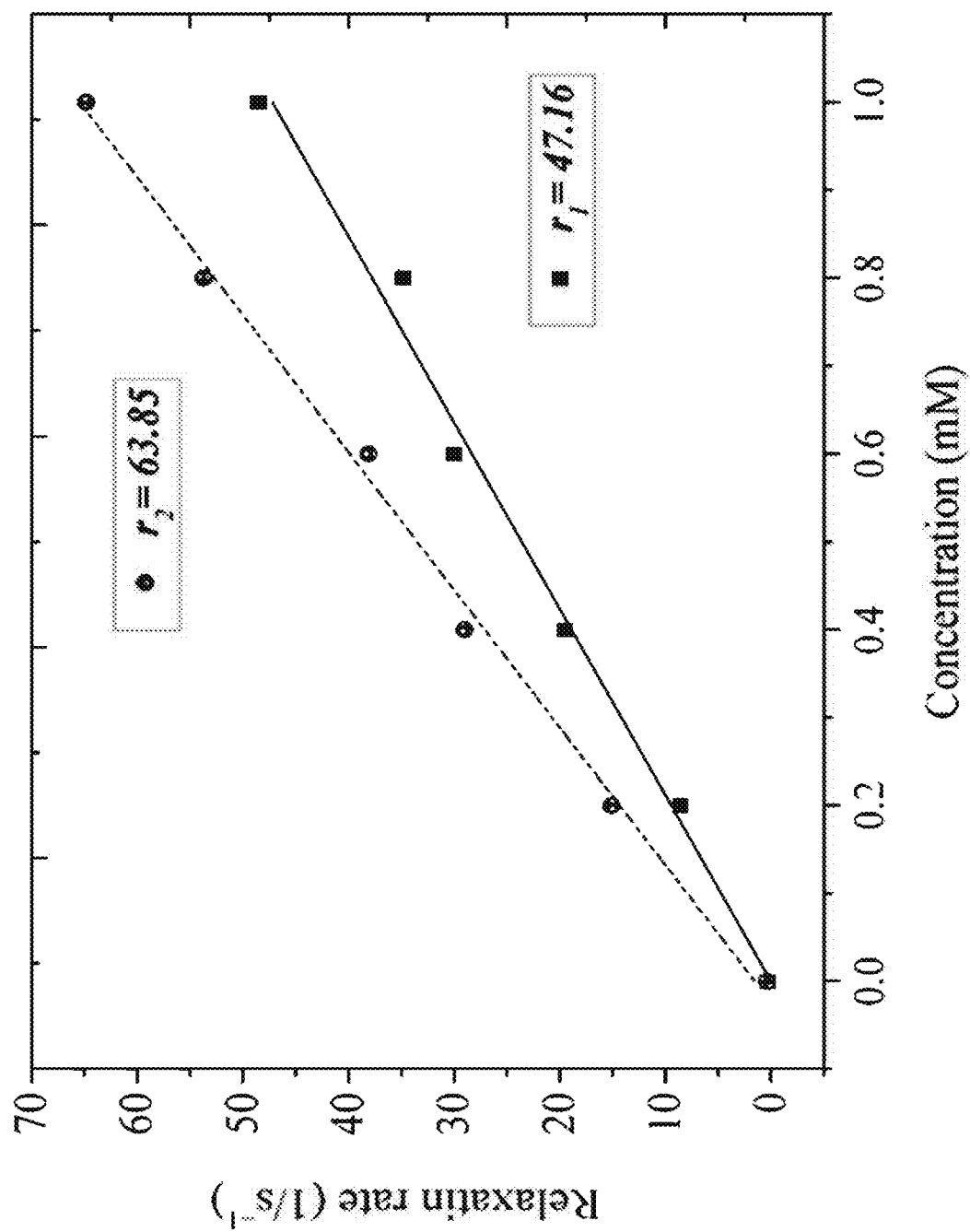
FIG. 3B is a plot showing the relaxivity ($r_1$ and $r_2$) of the polymer nanopcomposite materials disclosed herein.
Figure 4:
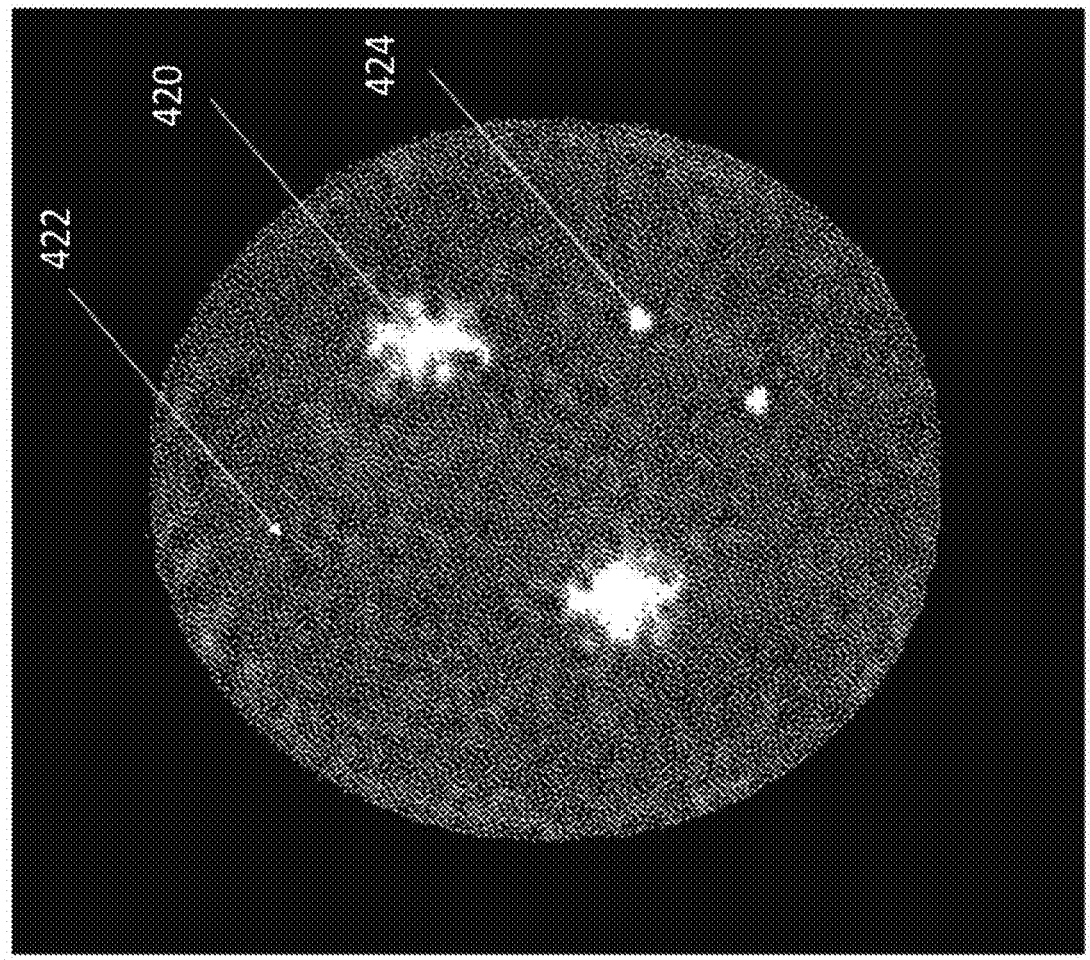
FIG. 4 is a coronal view of a T1-weighted MRI image showing in situ cross-linked nanocomposite marker 20 in a gelatinous phantom 22.
Figure 5A:
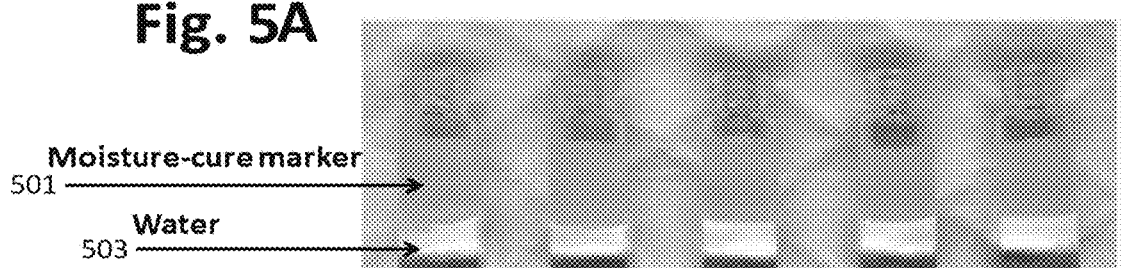
FIG. 5A is bright field image of 5 ml glass vials that contain ~2 ml water on the bottom of the vials and ~2.5 ml of the 3D cured nanocomposite containing different concentrations of gadolinium oxide nanoparticles.
Figure 5B:
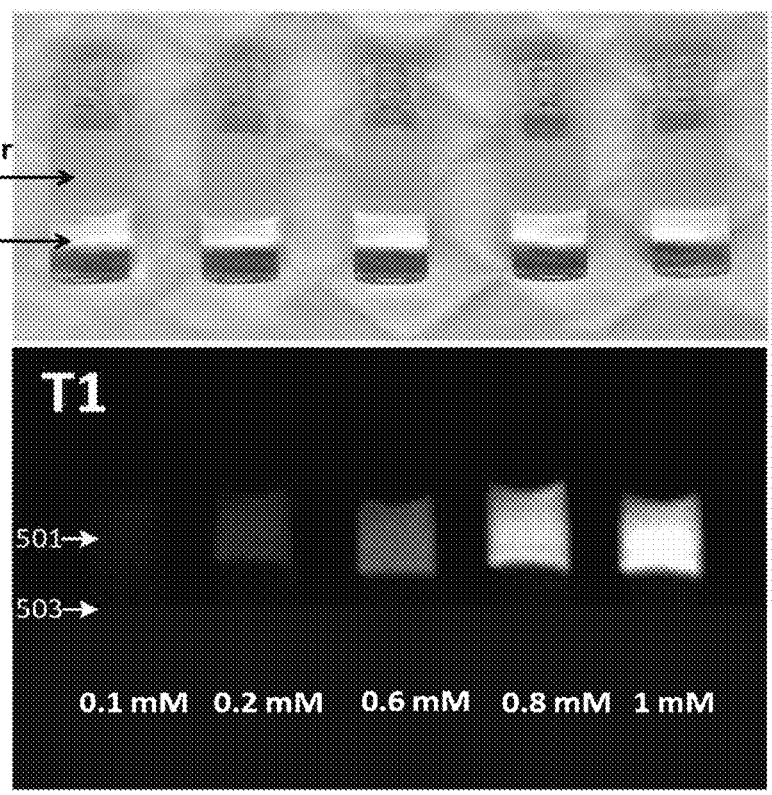
FIG. 5B is a T1-weighted MRI image of 5 ml glass vials that contain ~2 ml water on the bottom of the vials and ~2.5 ml of the 3D cured nanocomposite containing different concentrations of gadolinium oxide nanoparticles, the 3D cured nanocomposite indicating a linear change in MRI contrast as a function of nanoparticle concentration.
Figure 5C:
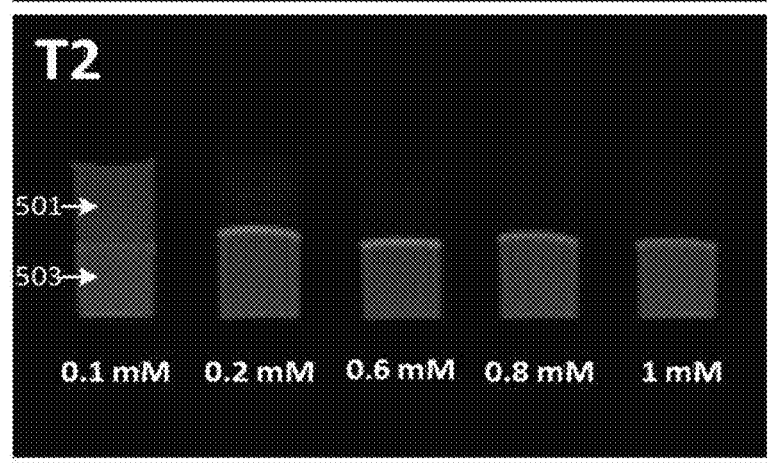
FIG. 5C is a T2-weighted MRI image of 5 ml glass vials that contain ~2 ml water on the bottom of the vials and ~2.5 ml of the cross-linked nanocomposite marker containing different concentrations of gadolinium oxide nanoparticles.

Paramagnetic nanoparticle, which are gadolinium-based nanoparticles, have 7 unpaired electrons in their valence orbitals, leading to a high magnetic moment (7.94 µB). The electron spin relaxation time of Gadolinium is long (~1× $10^{-9}$ s), maximizing dipole-dipole interactions of electrons and $^1H$ protons in the vicinity of the gadolinium nanoparticles. This increases the relaxation rate of nearby $^1H$ proton nuclei spin per concentration of the nanoparticles incorporated. Gadolinium-based nanoparticles are utilized in the present example. Gadolinium nanoparticles shorten T1 whereby the marker show positive contrast (appear bright) 310 compared to surrounding tissues 312, as shown in FIG. 3A. FIG. 3B is an exemplary plot showing the relaxivity ($r_1$ and $r_2$) of the polymer nanopcomposite materials disclosed herein. The paramagnetic nanoparticle depicted in the plot is gadolinium oxide nanoparticles (~5 nm). Various concentration (0-1 mM) were used to measure the relaxivities of the markers which is calculated by measuring the relaxation rate of $^1H$ (longitudinal and transversal relaxation), normalized to the concentration of paramagnetic element in the marker composition (mM of gadolinium). The markers show an $r_1$ 47.16 $mM^{-1}$ $s^{-1}$ which is significantly higher than commercial gadolinium—chelates contrast agents (<7 $mM^{-1}$ $s^{-1}$). These interactions shorten the spin-lattice relaxation time (T1) of the $^1H$ protons within the nanocomposite polymer. This in turn results in an enhancement effect (also known as positive contrast) in the MRI signal 420 of the cross-linked nanocomposite compared to surrounding tissues 422 (FIG. 4). In FIG. 4, the markers were also made into small (1 mm×5 mm; d×1 mm) fiducials 424 using gadolinium oxide nanoparticle concentration of 0.8 mM. The cross-linked nanocomposite marker adheres and conforms to its surroundings. Both markers are clearly visible on MRI. Therefore, the 3D cured nanocomposite 501 markers disclosed herein have opposite MRI signals to that of the surrounding tissues 503, thus making the markers clearly distinguishable on T1 (FIG. 5B) and T2 (FIG. 5C) MRI as the concentration of the nanoparticles increase. FIG. 5A is a visible light image of test vials. The enhancement in signal (i.e., contrast) can be further amplified by using ultra-small nanoparticles particles size (<5 nm). This is due to the significantly increased surface-area-to-volume ratio when using nanoscale size materials.

For example, paramagnetic nanoscale materials used herein have several unique advantages for biomedical imaging in that nanoparticles can concentrate a large number of magnetic ions in a small volume thus offering a very high T1 and T2 (FIG. 5A, FIG. 5B, and FIG. 5C) signal and as a result, a significant improvement in signal-to-noise ratio. For example, a gadolinium-based nanoparticle as described herein have a very high T1 and T2 relaxivities (> of 40 $mM^{-1} s^{-1}$) that can easily be tuned by changing the diameter of the nanoparticles compared to a relaxivity of <7 $mM^{-1} s^1$ for commercial gadolinium chelates/compounds including Gd-BOPTA (gadobenate dimeglumine, MultiHance), Gd-DO3A-Butrol (gadobutrol, Gadovist®/Gadavist®), Gd-DOTA (gadoterate meglumine, Dotarem®), Gd-DTPABMA (gadodiamide, Omniscan®), Gd-DTPA-BMEA (gadoversetamide, OptiMARK®), Gd-EOB-DTPA (gadoxetic acid disodium, Primovist®/Eovist®), Gd-HP-DO3A (gadoteridol, ProHance®), and MS-325 (gadofosveset trisodium, Ablavar®). This is mainly due to the nanometer size of the materials which render them (i) large fraction of surface atoms; (ii) high surface energy; (iii) spatial confinement; (iv) reduced imperfections, which do not exist in the corresponding bulk materials. The utility of paramagnetic nanoparticles over corresponding compounds/chelates have been shown in the literature. See Faucher L et al., 2012 Rapid Synthesis of PEGylated Ultrasmall Gadolinium Oxide Nanoparticles for Cell Labeling and Tracking with MRI ACS Applied Materials & Interfaces 4 4506-15 and Courant T, Et et al., 2012 Hydrogels Incorporating GdDOTA: Towards Highly Efficient Dual T1/T2 MRI Contrast Agents Angew. Chem. Int. Ed. 51 9119-22, each incorporated herein in its entirety.

In some embodiments of the biocompatible curable composition, the second nanoparticle is a radio-isotope seed. The radio-isotope seed is a radio-isotope encapsulated in a container known as a seed. The container may be described as a tube-like titanium shell that is about the size of a grain of rice. A radio-isotope seed may contain, but is not limited to Iodine-125, Cesium-131, Palladium-103 or Praseodymium-142. The container may be 1 mm to 5 mm or 2 mm to 4 mm in length and a diameter of the cross section may be 0.5 µm to 1.5 mm, 5 µm to 1 mm, 50 µm to 900 µm, or 500 µm to 750 µm. The container may be an elongated pellet shape or spherical shape. A radiation dosage of a radio-isotope seed may be a low dose rate, a medium dose rate, a high dose rate or a pulsed dose rate. The low dose rate may be described in Grays/hour of about 0.1 to 2, about 0.5 to 1.5, or about 0.75 to 1. The medium dose rate may be described in Grays/hour of about 2 to 12, about 4 to 10, or about 6 to 8. The high dose rate may be described in Grays/hour of about 12 to 40, about 20 to 30, or about 22 to 25. The pulsed dose rate may be at the low dose rate, medium dose rate or high dose rate and may be an interrupted application of the low dose rate, medium dose rate or high dose rate at about 1/day-24/day, about 2/day-20/day, about 5/day-18/day, about 8/day-15/day, or about 10/day-12/day.

In some embodiments of the biocompatible curable composition, a microbubble may be inside the biocompatible curable composition and the 3D cured nanocomposite thus enabling the biocompatible curable composition and the 3D cured nanocomposite to be visible by ultrasound. Microbubbles are small gas-filled microspheres that have specific acoustic properties that make them useful as a contrast agent in ultrasound imaging. First-generation microbubbles are room air microspheres. Improved stability in microbubbles may be achieved by stabilizing microbubbles with a thin shell, like albumin (Albunex) or galactose palmitic acid (Levovist). Further improved stability and contrast in ultrasound may be achieved by injected into the biocompatible curable composition and the 3D cured nanocomposite with microbubbles filled with a heavy-molecular-weight gas like e.g. sulphur hexafluoride. Surfactants, sonicated albumin and (phospho)lipids are used to improve stabilization of the shell of a microbubble by those familiar in the art. For example, Sonovue, a second-generation contrast agent, is a phospholipid coated, sulphur hexafluoride gas containing microbubble used in diagnostic imaging. These microbubbles have much smaller diameters than ambient air-filled bubbles (about 2.5 µm).

In some embodiments of the biocompatible curable composition, a shape of the nanoparticle may include, but is not limited to nanospheres, nanorods or nanoplates. In some implementations of the method, the metallic nanoparticle is modified by at least one of an organic ligand, a coupling agent, and a surfactant. For example the metallic nanoparticle may aggregate and an organic ligand molecule bound to the nanoparticle surface may prevent the aggregation of the nanoparticles. The organic ligand molecules may first have to be bound to the particle surface by some attractive interaction, either chemisorption, electrostatic attraction or hydrophobic interaction, most commonly provided by a head group of the ligand molecule. Various elements and ions possess a certain affinity to inorganic surfaces, such as thiol to gold. The affinity of certain elements and ions may further depend on the solvent environment in which a nanoparticle exists. Exemplary functional groups include, but are not limited to thiols, disulfides, amines, ammonium ions, carboxylic acids, phosphines, phosphates, carboxylates, silanes, sulfonates, amides and phosphonates. Organic ligands may include polar ligands, non-polar ligands, amphipathic ligands, or combinations thereof. For example the organic ligands may be, but are not limited to thiol ligands (thiolated polyethylene glycol, mercaptosuccinic acid, dodecane thiol), phosphorous ligands (tri-n-octylphosphine, 1,2-Bis(diphenylphosphino)ethane, (2,2'-bis(diphenylphosphino)-1,1'-binaphthyl), or nitrogen-based ligands (4-dimethylaminopyridine, porphyrins, pyridyl groups, 1-ethyl-3-(3-dimet 1-ethyl-3-(3-dimethylaminopropyl)carbodiimide, phenylaminopropyl-carbodiimide, imidazole derivatives). For example, the coupling agent or adhesion promoter may be, but is not limited to (2-(3,4-epoxycyclohexyl)ethyl)trimethoxysilane, 3-aminopropyltriethoxysilane, n-propyltriethoxysilane, poly(hydroethyl) acrylate. The silane coupling agents in the preceding exemplary list contain reactive functional groups of methoxy or ethoxy that can react with inorganic materials including silica and metal oxides. With the presence of methoxy or ethoxy functional groups, hydroxyl bonds may form with the metal adhesion. For example, the surfactant may be, but is not limited to thiol-terminated homopolymer of polystyrene, thiol-terminated 2-vinylpyridine, cetyltrimethylammonium bromide. The surfactant may not be covalently bound to the nanoparticle but may be interacting through a moderate electrostatic charge, induced dipole interaction, or other molecular interactions familiar to those in the art. An exemplary variable that may be a cause of an induced interaction is the nanoparticles isoelectric point or the pH of the surrounding solution.

In some embodiments of the biocompatible curable composition, the nanoparticles may be combined with the biocompatible curable composition directly or dispersed in a polar or non-polar solvent before combining with the biocompatible curable composition to facilitate the dispersion of the nanoparticles. Exemplary solvents for dispersing nanoparticles include but are not limited to water, methanol, isopropanol, hexane or toluene.

In some embodiments, the nanoparticles of the present disclosure may further enhance a mechanical property of the nanocomposite marker by acting as molecular bridges in the moisture cross-linked polymer matrix, hence significantly improving the mechanical properties such as tensile strength and elongation at break. The molecular bridges may be formed through intermolecular interactions with functional groups of the polymer backbone, functional groups on a side chain of the polymer, or both.

Returning to the method of implanting and detecting the above described biocompatible curable composition, the injecting into a subject may be via a syringe or a narrow tube. The syringe may have a gauge of 27-20, 26-22, 25-24 and the narrow tube may have a diameter of 0.4 mm-1 mm, 0.5 mm-0.9 mm, 0.6 mm-0.8 mm, or 0.7 mm-0.75 mm. The biocompatible curable composition may be injected nearby to a tumor, a tissue of interest or both, such that the biocompatible curable composition is contacting the border of the tumor, the tissue of interest, or both. The border of the tumor may be well-defined from the non-tumor tissue of the subject or may be intermingled with non-tumor tissue and difficult to discern. The border of a tumor may defined as an edge of the tumor or tumor epithelium (i.e. outer layer of cancerous cells of the tumor). However, during surgical procedures, the border of the tumor may be defined as the edge or border of the tissue removed in cancer surgery. The border of the tumor or the margin may be described as negative or clean when a pathologist finds no cancer cells at the edge of the tissue from which the tumor was excised, suggesting that all of the cancer has been removed. The margin is described as positive or involved when the pathologist finds cancer cells at the edge of the tissue, suggesting that all of the cancer has not been removed. The distance from a tumor, a tissue of interest, or both may be from direct contact up to 2 cm from a tissue/tumor, direct contact up to 1 mm, direct contact to 5 mm, or direct contact to 1 mm. Contacting may be defined as enabling the biocompatible curable composition having hydrolysable functional groups, as described herein, to crosslink to a molecule on a surface of the tumor, the tissue of interest, or both. The crosslinking between the biocompatible curable composition and the tumor and/or the tissue of interest is as described herein. The crosslinking between the biocompatible curable composition and the tumor and/or the tissue of interest may occur before the crosslinking of an interior of the biocompatible curable composition, simultaneously with the crosslinking of an interior of the biocompatible curable composition, or after the crosslinking of an interior of the biocompatible curable composition. The crosslinking occurs upon exposure to moisture or an aqueous solution. The aqueous solution may be water, an aqueous solvent mixture including ethanol, methanol, or isopropanol, or biological fluids such as urine, blood, mucus, bile, stomach acid, saliva, or tears.

In practice, the biocompatible curable composition may be packed in a syringe under inert conditions and then sealed inside an appropriate air-tight bag/box. A physician may then insert the needle and inject the biocompatible curable composition into or near tissues (e.g., prostate or breast). The syringes and needles used for injection must be approved by any regulatory (e.g., FDA) for medical use. It may be preferred that the biocompatible curable composition is injected through a bubble-free prime syringes that expel the air from the syringe (e.g., Hamilton® syringes). The volume of the injected biocompatible curable composition may depend on the biological target (e.g., lung, breast, prostate, soft tissues etc). In order to achieve optimum imaging signal and cure-rate, the volume used thereof can be, but not limited to 0.25 ml-5 ml, 0.5 ml-4 ml, 1 ml-3 ml, or 2 ml-2.5 ml.

Upon exposure to the aqueous solution or moisture the biocompatible curable composition crosslinks to form the 3D cured nanocomposite. The implantation of the 3D cured nanocomposite occurs via the crosslinking of the hydrolysable functional groups with the surface of the tumor and/or the tissue of interest by crosslinks as described herein. The crosslinks may be covalent bonds (i.e. amide, esters, disulfide), but may also include non-covalent bonds such as electrostatic interaction, hydrogen bonding, and monovalent and polyvalent metal interactions as described herein.

Following loading the biocompatible curable composition with paramagnetic nanoparticles and injection 214 (FIG. 2A) into tissues, the moisture inside tissues, exemplified in FIG. 2B as a glass of water 200, immediately initiates a hydrolysis reaction where reactive silanol groups (Si—OH) are formed 216. The reactive silanol groups then crosslinked with each other to form a three dimensional polymer structure (3D cured nanocomposite) with siloxane linkages (—Si—O—Si—) 216. The cross-linked marker could potentially be excised from tissues 218 (FIG. 2C).

Upon injecting the biocompatible curable composition, the subject may be imaged by at least one of MRI, CT, ultrasound, or X-ray. The metallic nanoparticles in the biocompatible curable composition, as described herein, enable the polymer to be visible under various diagnostic imaging modalities, particularly MRI, CT and ultrasound. The 3D cured nanocomposite may have improved contrast in images relative to the biocompatible cured composition by about 1% to 60%, about 5% to 50%, about 10% to 40%, or about 20% to 30%. Image contrast may be calculated through the use of software such as ImageJ, Adobe® Photoshop, or an image processing software familiar to those in the art to determine percentage difference in contrast. Tissue characteristics can be imaged by determining the concentration (or density) of hydrogen ($H^1$) protons within the tissue and weighting (T1 or T2-weighted imaging). For example, tissues with high proton contents (e.g., fat) will produce strong signals and have a bright appearance on T1-weighted images. Therefore, the MR image is an image of $H^1$ protons. When tissues that contain hydrogen (i.e., protons) are subjected to a magnetic field, some of the proton nuclei spins align in the same direction as the magnetic field. This alignment produces the magnetization in the tissue, which then emits a radio-frequency signal. Tissues that do not have an adequate concentration of hydrogen are not visible on MRI. Medical radiography is done using X-rays formed in an X-ray tube. When directing an X-ray toward an object, a certain amount of X-ray is absorbed by the object, which is dependent on the particular density and composition of that object. The X-rays that pass through the object are captured behind the object by a detector (either photographic film or a digital detector). The detector can then provide a superimposed 2D representation of all the object's internal structures. CT makes use of computer-processed combinations of many X-ray images taken from different angles to produce cross-sectional (tomographic) images (virtual "slices") of specific areas of a scanned object, allowing the user to see inside the object without cutting. Ultrasound, or medical sonography, is an ultrasound-based diagnostic medical imaging technique used to visualize muscles, tendons, and many internal organs, to capture their size, structure and any pathological lesions with real time tomographic images. Ultrasound has been used by radiologists and sonographers to image the human body and has become a widely used diagnostic tool.

The 3D cured nanocomposite may contour around the tumor, the tissue of interest, or both enabling an image to detect an edge or the border of the specimen. In some implementations of the method, the imaging further includes registering the image of the three-dimensional cured nanocomposite at the border of a tumor, a tissue of interest, or both. Image registration is the process of transforming images acquired at different time points, or with different imaging modalities, into the same coordinate system. It facilitates surgical planning by combining images with important complementary structural and functional information to improve the information basis on which a surgeon makes critical decisions. Thus in surgical application registering the images allows the images to be correlated to assist a surgeon to navigate a surgical bed and treat or resect the correct tumor, tissue of interest, or both. Further, the 3D cured nanocomposite may be a fiducial and visual marker for a surgeon.

The biocompatible curable composition may be employed as a fiducial marker, which may be implanted using an FDA approved delivery system such as those used to implant conventional gold fiducial markers. Examples of deployment systems are described in assigned patent pub. Nos: U.S. Pat. Nos. 8,838,208 B2, 9,042,964 B2 and US 20150196369 A1. See U.S. Pat. No. 8,838,208 B2, Fiducial deployment needle system, Shay Lavelle et al, Sep. 16, 2014; U.S. Pat. No. 9,042,964 B2, System and method for fiducial deployment via slotted needle, Richard W. Ducharme et al, May 26, 2015; and US 20150196369 A1, System, method and device employing fiducials for medical intervention, Neil Glossop, Jul. 16, 2015, each incorporated herein by reference in its entirety.

In some implementations of the method, the biocompatible curable composition may be employed as a target volume surrogate to mimic a target organ as the target organ moves in a human body due to breathing and natural movements of surrounding organs to the target organ.

In some implementations of the method, the method further includes a second injecting of a radio-isotope seed into the three-dimensional cured nanocomposite after the injecting or after the imaging. The radio-isotope seed is as described herein. The 3D cured nanocomposite may guide a surgeon for placement of radio-isotope seeds for brachytherapy. Brachytherapy is a form of radiotherapy where a sealed radiation source is placed inside or next to the area requiring treatment (i.e. a tumor).

The composition described by the present disclosure may be used as a tissue spacer in radiotherapy; for example, to separate the rectum from the prostate during prostate radiotherapy. The prostate is situated without a significant distance to the rectal wall and radiotherapy guidelines require safety margins around the prostate of approximately 5-10 mm (depending on several factors such as patient positioning). Therefore, the anterior rectal wall is always included in the treatment planning volume. The insertion of a tissue spacer between the prostate and rectum is an increasingly used technique to create a significant distance between the prostate and rectum and thus exclude the rectum from the treatment planning volume. This also avoids unnecessary radiation dose to the rectum wherein radiation often results in serious risk of injury, including severe radiation-induced rectal burns. The biocompatible curable composition may be injected between the rectum and prostate (preferably >0.5 ml) prior to radiotherapy under X-ray or transrectal ultrasound-guidance. The composition thereof would cross-link in situ and act as a rectum-prostate spacer and also, a positive T1-weighted MRI marker. Assigned patent application pub. No. U.S. Pat. No. 8,383,161 B2 ('161), discloses an organic radiopaque polyethylene glycol (PEG) hydrogel that is used as a spacer in radiotherapy. Reference '161 describes a hydrogel that is covalently bonded to radiopaque iodine rendering the hydrogel visible on CT. See U.S. Pat. No. 8,383,161 B2, Radioopaque covalently crosslinked hydrogel particle implants, Patrick Campbell et al, Feb. 26, 2013, incorporated herein by reference in its entirety. However, previously described hydrogels have similar MRI contrast to that of tissues therefore cannot be used as a positive T1-weighted MRI marker.

The biocompatible curable composition of the present disclosure may further be employed as a brachytherapy strand, as described herein, embedded with a radio-isotope seed. The biocompatible curable composition may crosslink upon the addition of an aqueous solvent as described herein or exposure to ambient moisture to form a 3D cured nanocomoposite. The radio-isotope seed embedded within the biocompatible curable composition having formed into the 3D cured nanocomposite enables the radio-isotope seed to be visible by MRI for assistance during surgical implantation. Further the 3D cured nanocomposite is an elastomeric 3D cured nanocomposite as described herein, further protecting the brachytherapy strand from breakage during implantation. The brachytherapy strand may be a seed spacer adhesive agent.

In some embodiments of the brachytherapy strand, the biocompatible curable composition may coat the radio-isotope seed individually for implantation, enabling the individual radio-isotope seed to be visible by MRI.

The composition disclosed herein may be used as a spacer, strand material and a marker in MRI-guided brachytherapy commonly used to treat prostate cancer. Most commercial brachytherapy seeds contain solid and liquid-free radioactive Iodine-125, Cesium-131, Palladium-103 or Praseodymium-142 radioactive sources. These radioactive sources may be encased in a titanium seed, as described herein. Current brachytherapy seeds and spacer technologies involve attaching commercial radioactive seeds to a spacer material made from biocompatible/bio-absorbable materials. In some technologies, a liquid MR' or CT contrast agent is encapsulated in a biocompatible polymer and attached to brachytherapy seeds whereby the polymer act as a spacer and the encapsulated contrast agent acts as an imaging marker. Several brachytherapy strand designs have been disclosed in assigned patent application publications. See US 20140178297 A1, Seeds and Markers for Use in Imaging, Steven J. Frank et al, Jun. 26, 2014; US 20100324353 A1, Adhesive-stiffened brachytherapy strand, Kevin Helle, et al, Dec. 23, 2010; US 20090216063 A1, Bio-absorbable brachytherapy strands, Gary A. Lamoureux et al, Aug. 27, 2009; US 20120065454 A1, Tethered and/or visually coded brachytherapy devices and related methods, Andrew Karim Kader et al, Mar. 15, 2012; U.S. Pat. No. 8,795,146 B2, Implants including spacers for use in brachytherapy and other radiation therapy that resist migration and rotation, Gary A. Lamoureux et al, Aug. 5, 2014; U.S. Pat. No. 8,771,162 B2, Spacers for use in brachytherapy, radiotherapy, and other medical therapy, Gary A. Lamoureux et al, Jul. 8, 2014; U.S. Pat. No. 6,575,888 B2, Bioabsorbable brachytherapy device, Paul O. Zamora, Jun. 10, 2003, each incorporated by reference herein in its entirety.

Figure 6:
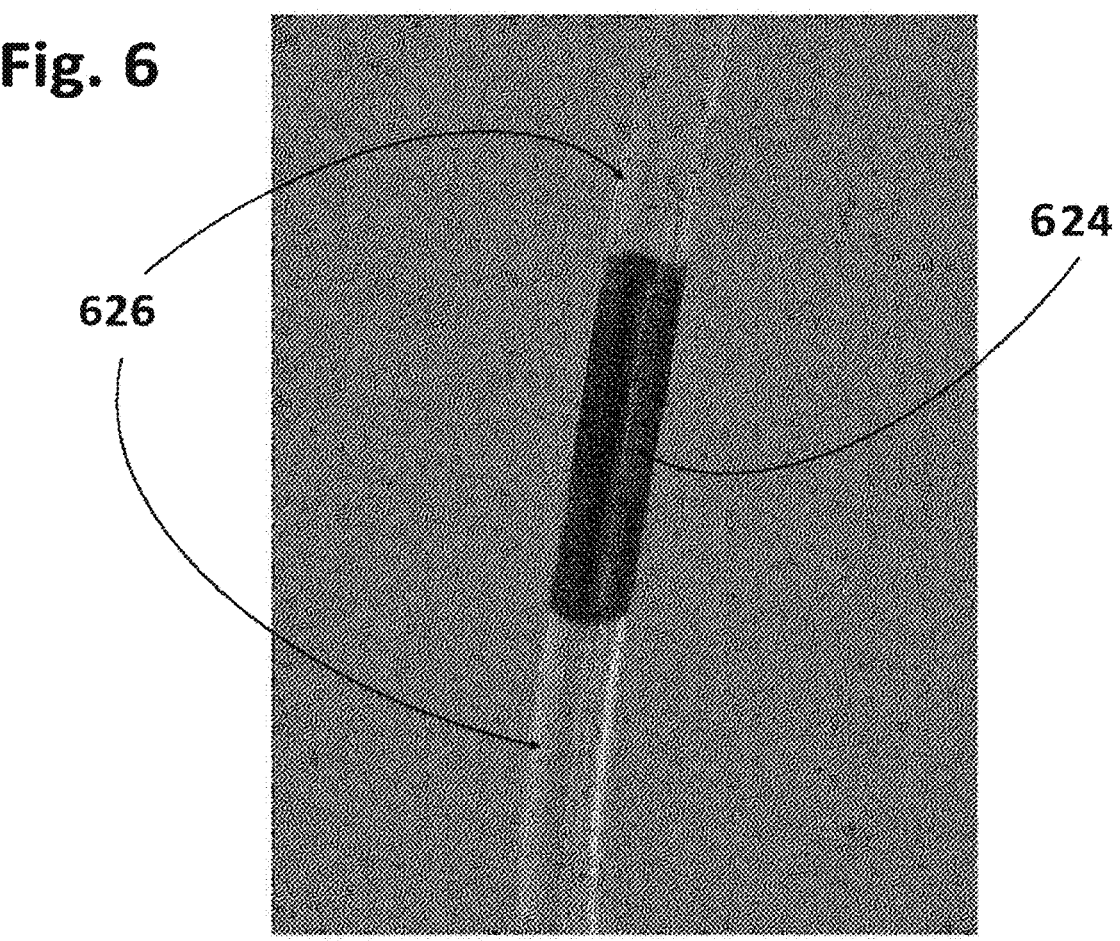
FIG. 6 is a microphotograph (1:1 magnification) of Iodine-125 seeds (0.8 mm×4.5 mm; d×1) 624 completely embedded in a 3D cured nanocomposite strand that acts as embedding agent, brachytherapy strand material, positive MRI marker, spacer and seed-spacer adhesive agent 626.

As shown in FIG. 6. More particularly, any commercial radioactive seeds 624 utilized in brachytherapy can be spaced and completely embedded within the nanocomposite strands 626 wherein the nanocomposite strand 626 function as: (1) embedding agent; (2) spacer; (3) positive MRI marker and (4) seed-spacer linking/adhesive agent. In more details, in FIG. 7A and FIG. 7B, the brachytherapy 3D cured nanocomposite strand disclosed herein 728 comprise (1) commercial brachytherapy radioactive seeds 730 (or pellets) and (2) embedding cross-linked nanocomposite marker 732 wherein the diameter 734 is identical to the diameter of commercial brachytherapy seeds, which is about 0.2 mm-1.0 mm, about 0.4 mm-0.9 mm, or preferably about 0.5 mm-0.8 mm. In more details, brachytherapy seeds can be separated by an integrated spacer 732 at any desired distance, for example the seeds may be spaced 3-6 mm apart and then completely embedded in the cross-linked nanocomposite marker 732 disclosed herein. The diameter 738 (FIG. 7B) is 0.3-1 mm (OD) wherein 0.1 mm coats both external walls 736 of the seed 730 and the same diameter of the integrated spacer 732 wherein the integrated spacer 732 has the same function as a part of the nanocomposite strand 626 pointed out in FIG. 6.

Referring to FIG. 7A and FIG. 7B, the brachytherapy seeds may be placed and spaced as per clinical indications in an embedding mold. The biocompatible curable composition may be poured over the seeds and left to cure via cross-linking under standard atmospheric conditions. This affords a cross-linked nanocomposite marker strand containing completely embedded brachytherapy seeds. The seed would be firmly locked within the polymer therefore minimizing the risk of breakage or migration inside the body.

Figure 8A:
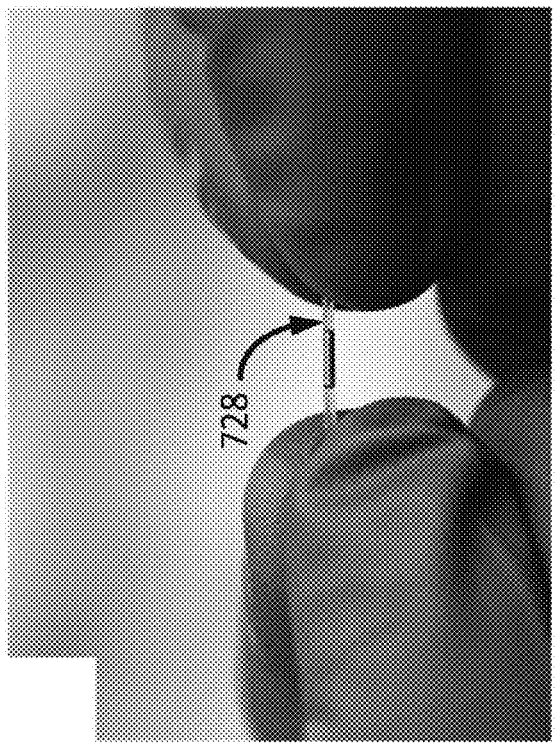
FIG. 8A is a microphotograph (1:1 magnification) of an embedded seed showing the durability of the cross-linked nanocomposite strand in resting state.
Figure 8B:
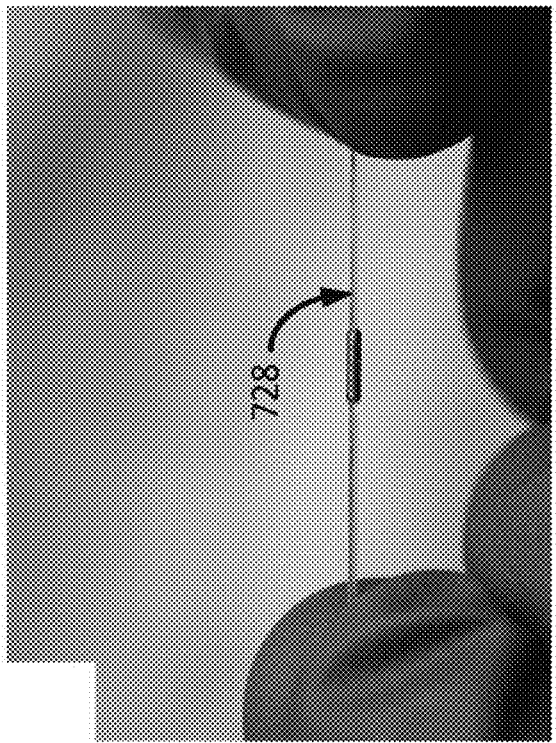
FIG. 8B is a microphotograph (1:1 magnification) of an embedded seed showing the durability of the cross-linked nanocomposite strand in stretched/elongated state.
Figure 9:
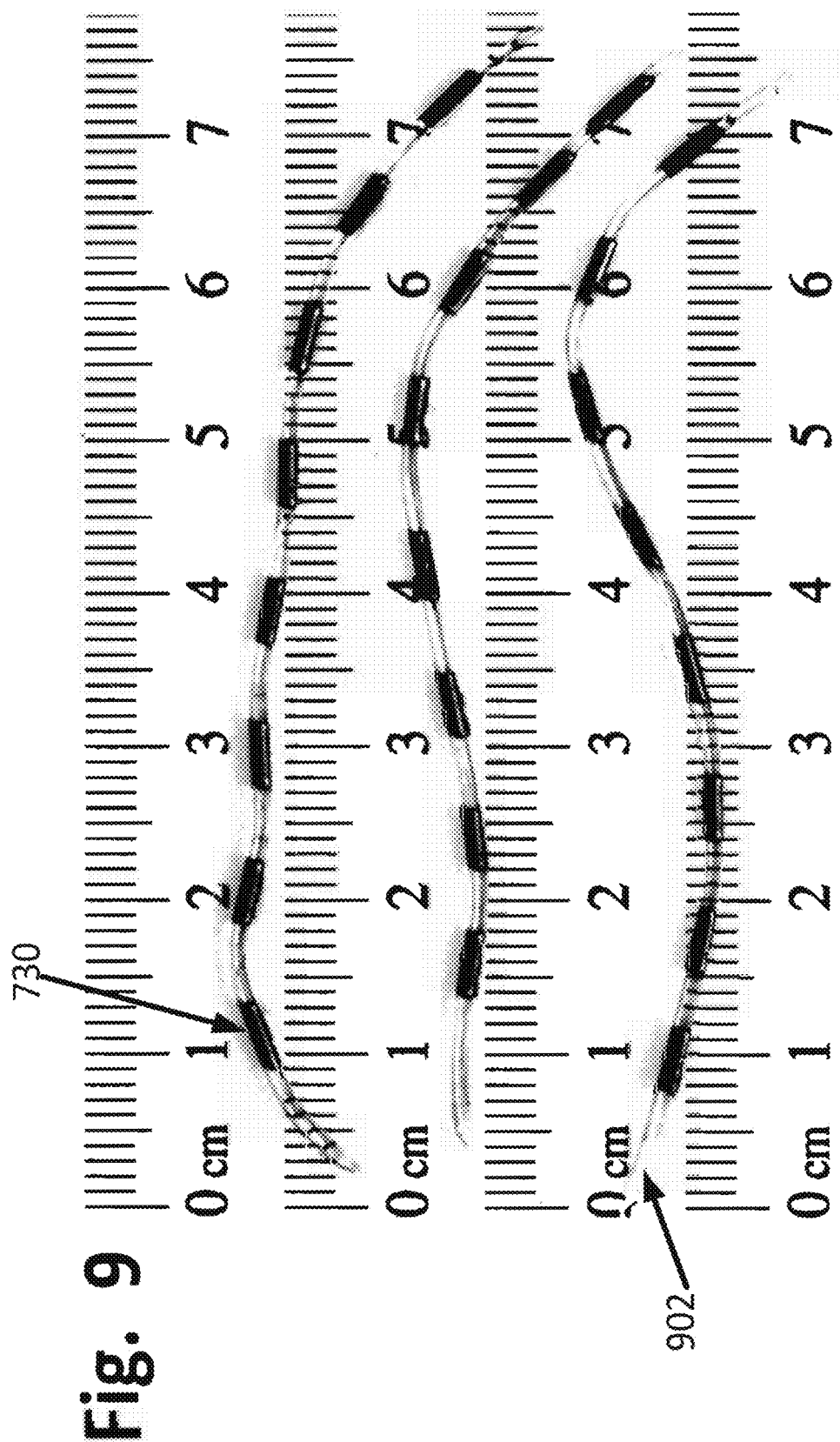
FIG. 9 is a microphotograph (1:1 magnification) of the embedded brachytherapy seeds 730 in the cross-linked nancomposite strands 902.
Figure 10:
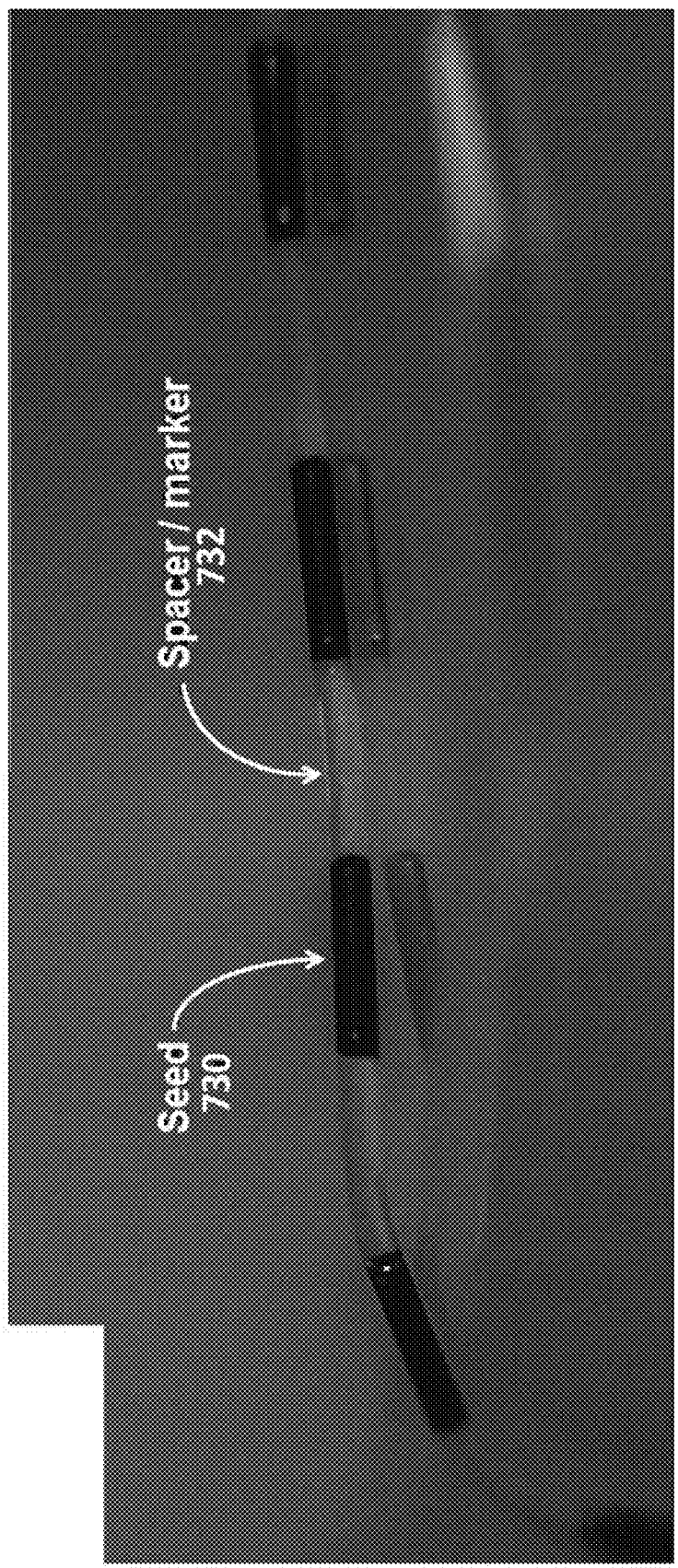
FIG. 10 is a photograph of the embedded brachytherapy seeds 730 in the cross-linked nanocomposite strand.
Figure 11A:
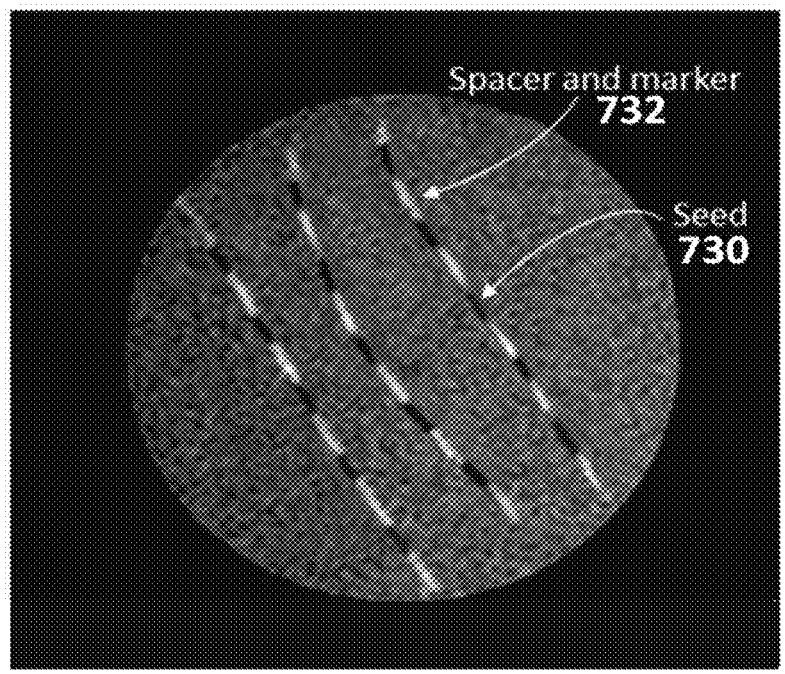
FIG. 11A is a coronal view of a T1-weighted MRI image of different sizes of embedded brachytherapy seeds in the 3D cured nancomposite material having a concentration of gadolinium oxide nanoparticles used here is 0.6 mM.
Figure 11B:
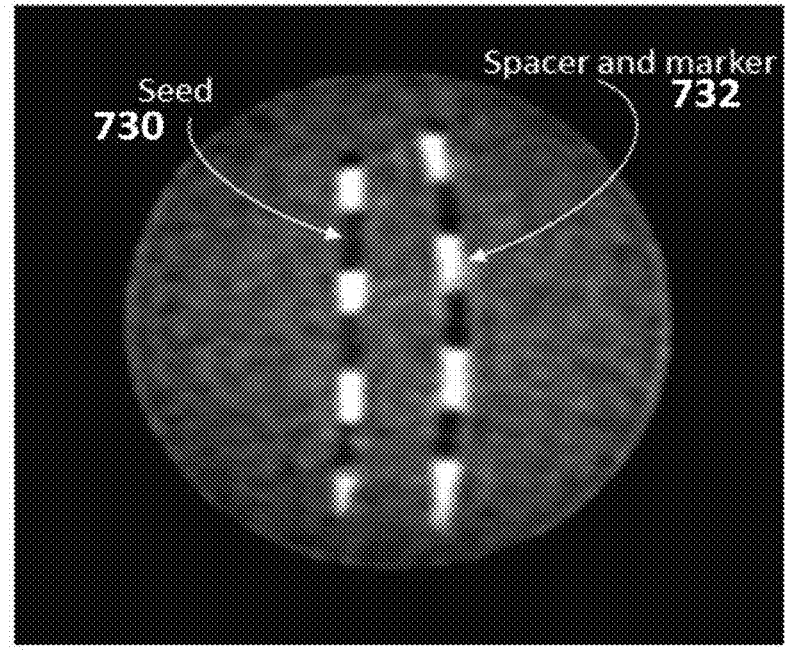
FIG. 11B is a coronal view of a T1-weighted MRI image of different sizes of embedded brachytherapy seeds in the 3D cured nancomposite material having a concentration of gadolinium oxide nanoparticles used here is 1.5 mM.

Any FDA approved brachytherapy seeds may be completely embedded in a biocompatible curable composition that acts as (1) strand material, (2) positive MRI marker (3) spacer and (4) seed-spacer linking/adhesive agent. The brachytherapy strand may lead to an improved durability against bodily fluids and corrosion. Polymer nanocomposites are more durable when at least one dimension of the reinforcement phase significantly enhances their fatigue properties, elasticity, and fracture toughness. Assigned patent pub. Nos. WO 2006073856 A2, WO2014040885 A3, U.S. Pat. No. 8,664,298 B1, WO2013154779 A1, WO2014159521 A1, WO2014144144 A1, WO2002024756 A2, US20140027116 A1 describe a number of polymer nanocomposites with enhanced properties. See WO 2006073856 A2, Durable high index nanocomposites for ar coatings, Christopher B Walker Jr et al, Jul. 13, 2006; WO 2014040885 A3, Polymer nanocomposite having switchable mechanical properties, Christoph Weder et al, May 30, 2014; U.S. Pat. No. 8,664,298 B1, Self-healing polymer nanocomposite coatings for use on surfaces made of wood, Runqing Ou et al, Mar. 4, 2014; WO 2013154779 A1, Nanocrystal-polymer nanocomposite electrochromic device, Delia Milliron et al, Oct. 17, 2013; WO 2014159521 A1, Gold nanorod/polymer nanocomposites and sensors based thereon, John F. Rabolt et al, Oct. 2, 2014; WO 2014144144 A1, Polymer nanocomposites, Allen David Clauss et al, Sep. 18, 2014; WO 2002024756 A2, Hydrophobically modified clay polymer nanocomposites, Dennis Paul Lorah et al, Mar. 28, 2002; and US20140027116 A1, Polymer nanocomposite, process for making and use of same, Radhika Suresh et al, Jan. 30, 2014, each of which is hereby incorporated by reference herein in its entirety. Assigned patent pub. No. WO2014132107 A1 discloses a magnetic polymer nanocomposite for adsorbing water molecules. See WO 2014132107 A1, Preparation and use of magnetic polymer nanocomposites, hevasahayam Arockiadoss, Sep. 4, 2014, incorporated herein by reference in its entirety. As shown in FIG. 8A and FIG. 8B, wherein the elongation at break percentage of the brachytherapy strand disclosed herein exceeds 300%. In other words, the nanocomposite strand (with seeds completely embedded) (FIG. 8A) may be stretch more than 3 times its original length without fracture or permanent deformation (FIG. 8B). This property would completely eliminate the risk of seed breakage, loss, or migration within the body. FIG. 9 depicts several exemplary brachytherapy seeds 730 in elongated strands 902. FIG. 10 depicts a close-up image of the brachytherapy seeds 730 and the spacer 732 in between seeds. FIG. 11A and FIG. 11B depicts an MRI image of the brachytherapy seed 730 (dark colored gaps) and light regions representing the spacer 732 to indicate the MRI contrast produced by the spacer 732.

Current brachytherapy marker technologies involve the encapsulation of commercial (or custom) contrast or therapeutic agents. Typical commercial contrast or therapeutic agents are prepared in aqueous solutions (i.e., water). The downside of using liquid encapsulation in implantable marker technologies is the potential of leakage of the liquid components. Assigned patent no. U.S. Pat. No. 8,821,835 B2 ('835) discloses several brachytherapy seed designs and also several strand designs wherein the strand or linker is made from an elastic polymer such as elastin-like peptides, polyhydroxyalkanoates (PHAs), poly(glycol-sebacate) or proteins, incorporated herein by reference in its entirety. '835 further describes several hollow polymer designs (non-nanocomposite materials) with multiple lumens wherein brachytherapy seeds and liquid therapeutic active agent/s or commercial contrast agents (or a mixture of both) may be enclosed in a single flexible strand. '835 also discloses several external strand surface modification designs to minimize migration of the strand within a subject's body. See U.S. Pat. No. 8,821,835 B2, Flexible and/or elastic brachytherapy seed or strand. Edward J. Kaplan, Sep. 2, 2014, incorporated herein by reference in its entirety. Another aspect of the present disclosure is the elimination of the liquid component from the system wherein the embedding nanocomposite thereof does not contain any liquid contrast agent/s. Instead, that is replaced by solid phase paramagnetic nanoparticles incorporated within the biocompatible curable composition that cures to a durable, deformable and liquid-free brachytherapy nanocomposite strand that functions as a positive MRI marker as well. The presently disclosed biocompatible curable composition may be an improved technology because it may eliminates the risk of chemical leakage within the body and simplifies manufacturing.

Figure 12:
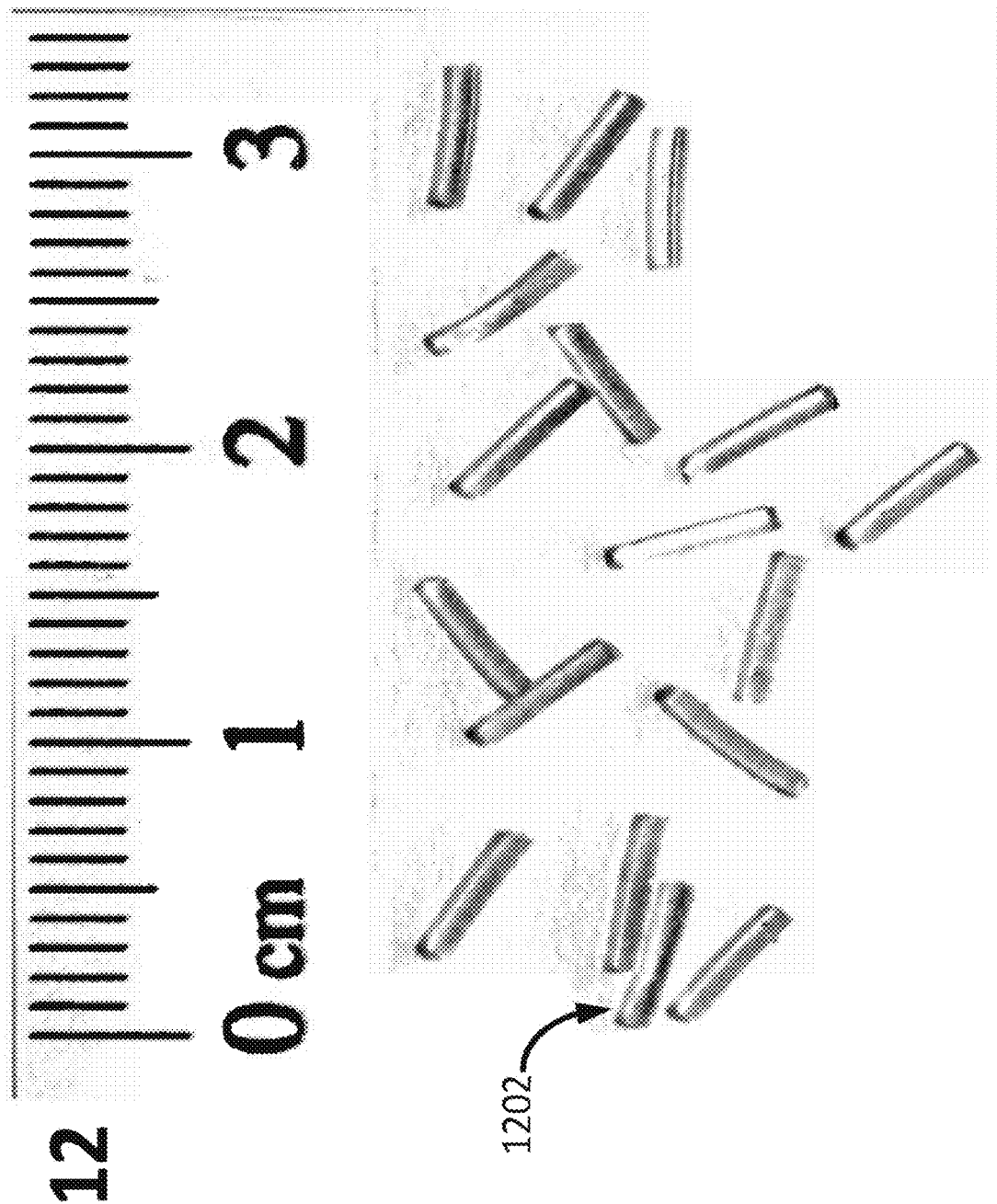
FIG. 12 is a microphotograph (1:1 magnification) of the fiducial markers.
Figure 13:
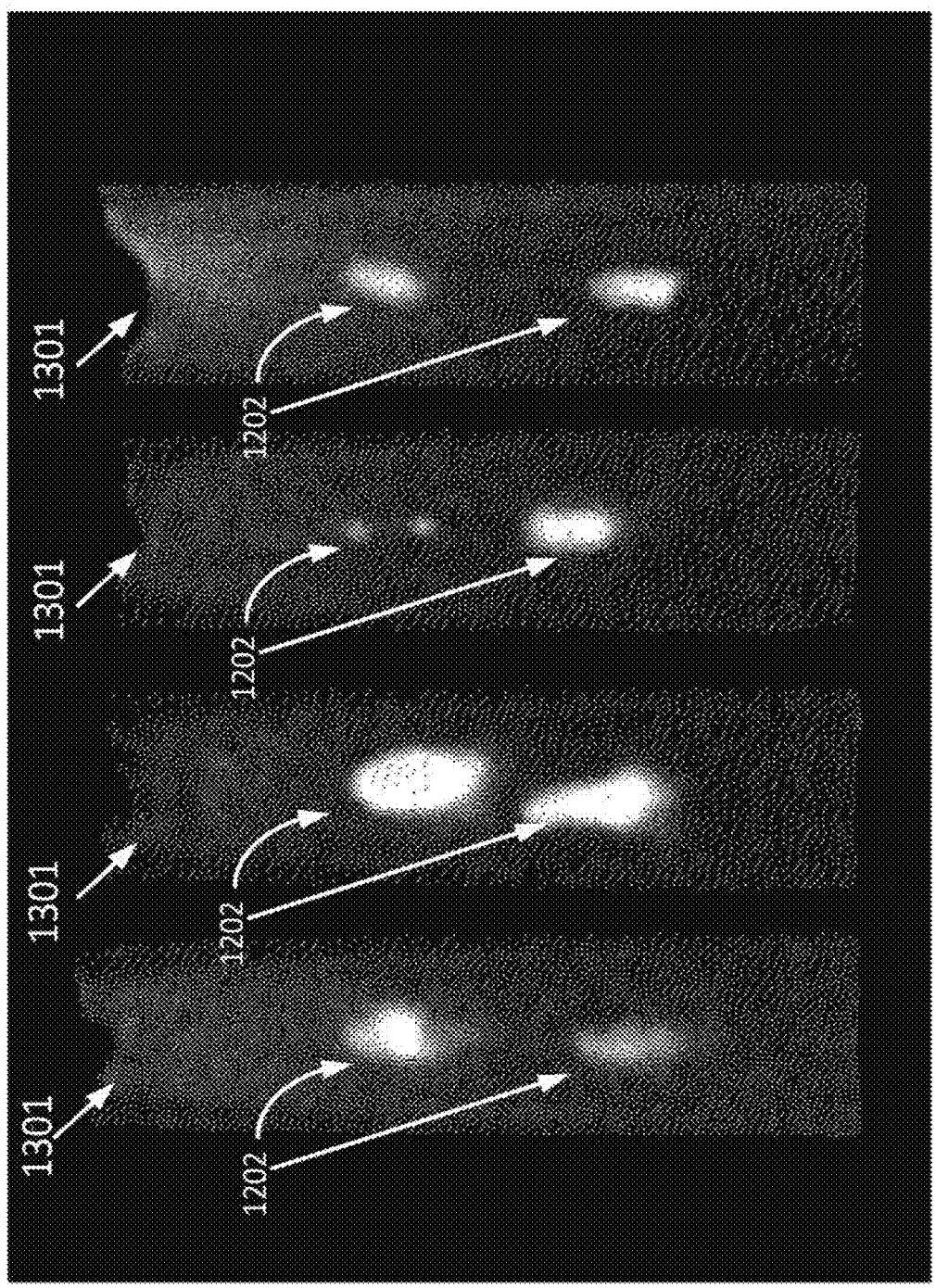
FIG. 13 is a coronal view of a T1-weighted MRI image of 20 ml glass vials filled with gelatinous materials and implanted with different shapes and sizes of the positive elastic fiducial markers.
Figure 14:
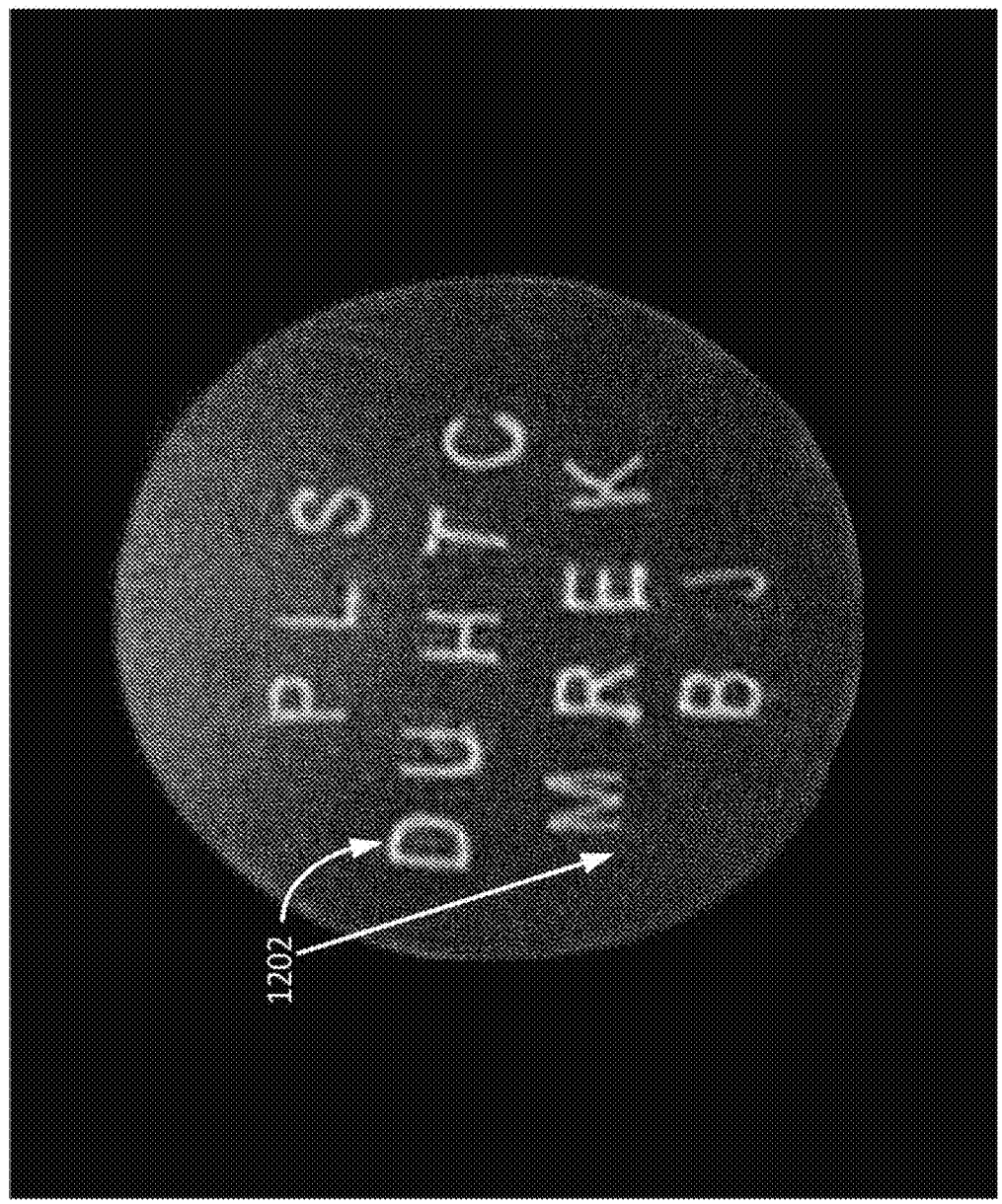
FIG. 14 is a coronal view of a T1-weighted MRI image an elastic positive MRI fiducial marker shaped in alphabetical letters and implanted in a gelatinous phantom.

In some embodiments, the composition disclosed herein may, for example, be used for MRI-guided radiotherapy and brachytherapy. The biocompatible curable composition can be molded and cross-linked ex vivo into an elastic fiducial marker 1202 with any implantable shape (FIG. 12). The markers can have any shape, for example, shaped in small cylinder with dimensions of but not limited to 1 mm in diameter and 5 mm in length 1202. Cross-linking mediated curing of the biocompatible curable composition can be achieved by exposing the composition to moisture or humidity or the use of none-moisture-cure systems. The resulting fiducial markers 1202 provide a positive MRI contrast and are clearly distinguishable from surrounding tissues 1301 (FIG. 13). For example, the fiducial marker may be employed for MRI-Linac radiotherapy systems or other systems where MRI-guidance is utilized, such as in prostate and breast cancer radiotherapy. FIG. 14 depicts the many shapes the fiducial marker 1202 may be shaped into.

In some embodiments, the external wall thereof can be modified to minimize migration of the fiducial marker after implantation. Such modifications may include but not limited to knurling or corrugation of the surface that help keep the marker in place post implantation. Knurling is a manufacturing process, typically conducted on a lathe, but may be by hand with the use of a hand-tool, whereby a pattern of straight, angled or crossed lines is cut or rolled into the material. Corrugating or Corrugation is the formation of wrinkles or folds or into alternating ridges and grooves into a surface or material, that may be accomplished by the action of scratching or pulling on the elastomer by hand to create ridges.

The invention claimed is:

1. A biocompatible curable composition comprising:
   an organic polymer comprising at least one hydrolysable functional group selected from the group consisting of a silane and an isocyanate;
   a solvent selected from the group consisting of hexane and toluene; and
   a metallic nanoparticle, wherein the metallic nanoparticle is at least one of a manganese-based nanoparticle and a gadolinium-based nanoparticle, and is dispersed in the organic polymer and the solvent at a weight percent relative to the total weight of the biocompatible curable composition of 0.1% to 30%;
   wherein the biocompatible curable composition crosslinks upon contact with an aqueous solution or moisture to form a three-dimensional cured nanocomposite.

2. The biocompatible curable composition of claim 1, wherein the metallic nanoparticle has at least one dimension of 1 nm-150 nm.

3. The biocompatible curable composition of claim 1, wherein a weight percent of the metallic nanoparticle is 2.5-30 wt. % relative to the total weight of the biocompatible curable composition.

4. The biocompatible curable composition of claim 1, wherein the metallic nanoparticle is modified by at least one of an organic ligand, a coupling agent, and a surfactant.

5. The biocompatible curable composition of claim 1, wherein the biocompatible curable composition and the three-dimensional cured nanocomposite are detectable by at least one imaging modality selected from the group consisting of magnetic resonance imaging, computed tomography, ultrasound, and X-ray.

6. The biocompatible curable composition of claim 1, further comprising a second nanoparticle comprising at least one of a paramagnetic element, a radio-isotope, a radio-opaque element, and a radio-opaque compound.

7. The biocompatible curable composition of claim 6, wherein the second nanoparticle is a radio-isotope seed.

8. The biocompatible curable composition of claim 1, wherein the three-dimensional cured nanocomposite is an elastomeric three-dimensional cured nanocomposite.

9. The biocompatible curable composition of claim 8, wherein the elastomeric three-dimensional cured nanocomposite is configured to crosslink a biological tissue via the hydrolysable functional group.

10. The biocompatible curable composition of claim 9, wherein the elastomeric three-dimensional cured nanocomposite has a Shore durometer hardness of 5 to 40 on a Shore durometer Type A scale, or a Shore durometer hardness of 40-100 on a Shore durometer Type OO scale.

11. The biocompatible curable composition of claim 1, wherein the organic polymer comprises at least one reacted form of a tetraethoxysilane, a methyltrimethoxysilane, a methyltriethoxysilane, an isobutyltrimethoxysilane, a phenyl trimethoxysilane, and a n-octyltriethoxysilane.

12. A brachytherapy strand consisting of:
    a biocompatible curable composition; and
    a radio-isotope seed;
    wherein the biocompatible curable composition comprises:
       an organic polymer comprising at least one hydrolysable or non-hydrolysable functional group selected from a silane and an isocyanate;
       a solvent selected from the group consisting of hexane and toluene; and
       a metallic nanoparticle, wherein the metallic nanoparticle is at least one of a manganese-based nanoparticle and a gadolinium-based nanoparticle, is dispersed in the organic polymer and the solvent at a weight percent relative to the total weight of the biocompatible curable composition of 0.1% to 30%, and is visible by MRI; and
    wherein the biocompatible curable composition is in the form of an elongated cylinder and crosslinks upon contact with an aqueous solution or moisture to form a three-dimensional cured nanocomposite having the radio-isotope seed embedded in the three-dimensional cured nanocomposite.

13. A method of detecting a border of a tumor, a tissue of interest, or both comprising:
    injecting a biocompatible curable composition into a subject and contacting the biocompatible curable composition with the border of a tumor, a tissue of interest, or both, wherein the biocompatible curable composition crosslinks upon exposure to an aqueous solution or moisture to form a three-dimensional cured nanocomposite, which is covalently bonded to the border of the tumor, the tissue of interest, or both; and
    imaging the three-dimensional cured nanocomposite by at least one of magnetic resonance imaging, computed tomography, ultrasound, and X-ray, wherein the border of the tumor, the tissue of interest, or both is detected;
    wherein the biocompatible curable composition comprises:
       an organic polymer comprising at least one hydrolysable functional group selected from the group consisting of a silane and an isocyanate;
       a solvent selected from the group consisting of hexane and toluene; and
       a metallic nanoparticle, wherein the metallic nanoparticle is at least one of a manganese-based nanoparticle and a gadolinium-based nanoparticle, and is dispersed in the organic polymer and the solvent at a weight percent relative to the total weight of the biocompatible curable composition of 0.1% to 30%.

14. The method of claim 13, wherein the metallic nanoparticle has at least one dimension of 1 nm-150 nm.

15. The method of claim 13, wherein the metallic nanoparticle is modified by at least one of an organic ligand, a coupling agent, and a surfactant.

16. The method of claim 13, wherein the three-dimensional cured nanocomposite is an elastomeric three-dimensional cured nanocomposite.

17. The method of claim 13, wherein the imaging comprises registering the image of the three-dimensional cured nanocomposite at the border of a tumor, a tissue of interest, or both.

18. The method of claim 13, further comprising injecting a radio-isotope seed into the three-dimensional cured nanocomposite after the injecting of the biocompatible curable composition or after the imaging.

19. The method of claim 13, wherein the biocompatible curable composition is employed in real-time target motion tracking in radiotherapy.

* * * * *